United States Patent
Wagner et al.

(10) Patent No.: US 6,548,451 B1
(45) Date of Patent: Apr. 15, 2003

(54) USE OF DERIVATIVES OF 2-OXOPYRROLE AS CROP PROTECTION AGENTS AND NOVEL 2-OXOPYRROLES

(75) Inventors: Oliver Wagner, Ludwigshafen (DE); Martina Otten, Ludwigshafen (DE); Karl-Otto Westphalen, Speyer (DE); Helmut Walter, Obrigheim (DE); Volker Harries, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/647,010

(22) PCT Filed: Mar. 24, 1999

(86) PCT No.: PCT/EP99/02006
§ 371 (c)(1),
(2), (4) Date: Jan. 24, 2001

(87) PCT Pub. No.: WO99/50243
PCT Pub. Date: Oct. 7, 1999

(30) Foreign Application Priority Data

Mar. 30, 1998 (DE) ........................... 198 14 040

(51) Int. Cl.$^7$ .................. C07D 207/44; A01N 43/36
(52) U.S. Cl. .................. 504/287; 424/409; 514/423; 548/531
(58) Field of Search .................. 548/531; 504/287; 514/423

(56) References Cited

U.S. PATENT DOCUMENTS

| | | | |
|---|---|---|---|
| 4,305,749 A | 12/1981 | Mildenberger | 71/67 |
| 4,749,795 A | 6/1988 | Pfenninger | 548/531 |
| 5,045,108 A | 9/1991 | Elbe | 71/94 |

FOREIGN PATENT DOCUMENTS

| | | |
|---|---|---|
| EP | 022 551 | 1/1981 |
| EP | 081 162 | 6/1983 |
| EP | 184 981 | 6/1986 |
| EP | 403 891 | 12/1990 |

OTHER PUBLICATIONS

Gorris, et al, 1995, VTT Symp., 148, 111–125.*
Pharmazie 47 (1992), H.10, 773–776, Lovren et al.
Chem.Abst.XP–002111153.
Chem.Abst XP–002111154.
J.Org.Chem.1992,57,6032–6037,Ramaiah et al.
Synthetische Versuche . . . Fischer et al., 73–103.

* cited by examiner

Primary Examiner—Joseph K. McKane
Assistant Examiner—Andrea D Small
(74) Attorney, Agent, or Firm—Keil & Weinkauf

(57) ABSTRACT

The invention relates to the use of 2-oxopyrroles of general formula (I) and their agriculturally usable salts as crop protection agents and to novel 2-oxopyrroles of formula (I). The substituents have the following meanings: $R^1$ represents aryl or heteroaryl and these radicals may carry one to five groups independently of each other or alternatively, the aryl or heteroaryl radical forms a bicyclical system with a fused-on phenyl ring, a fused-on $C_3$–$C_6$ carbocyclic compound or a 5- or 6-membered heterocyclic compound and $R^2$ represents $C_2$–$C_6$-alkyl or aryl or heteroaryl, $COOR^3$ or $CONR^3R^4$, $R^3$ and $R^4$ representing, independently of each other, hydrogen, $C_1$–$C_6$-alkyl, $C_2$–$C_6$-alkenyl, $C_3$–$C_7$-cycloalkyl or $C_2$–$C_6$-alkyl-aryl which can optionally be partially or fully halogenated or can carry one to three substituents chosen from the following: $C_1$–$C_4$-alkoxy, $C_1$–$C_4$-halogenalkoxy, $C_1$–$C_4$-alkylthio, $C_3$–$C_7$-cycloalkyl, $C_5$–$C_7$-cycloalkenyl.

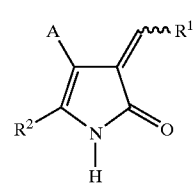

(I)

6 Claims, No Drawings

USE OF DERIVATIVES OF 2-OXOPYRROLE AS CROP PROTECTION AGENTS AND NOVEL 2-OXOPYRROLES

This application is a 371 of PCT/EP99/02006 Mar. 24, 1999.

The present invention relates to the use of 2-oxopyrrole derivatives of the formula I as crop protection agents

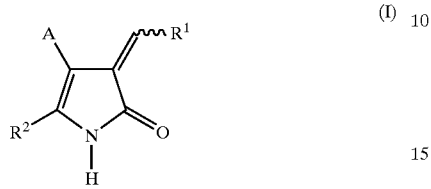

Furthermore, the invention relates to novel 2-oxopyrrole derivatives of the formula I.

2-Oxopyrroles of the formula I in which $R^1$ is phenyl, 4-dimethylaminophenyl or 2-nitrophenyl, $R^2$ is methyl and A is $COOC_2H_5$ are known from Z. Physiol. Chem. 132 (1924), 72. A possible use as crop protection agents is not mentioned.

It is an object of the present invention to provide compounds which are active as crop protection agents.

We have found that this object is achieved by the use according to the invention as claimed in claim 1.

Some of the 2-oxopyrrole derivatives to be used according to the invention are novel and as such also form part of the subject matter of the invention.

Preferred embodiments of the invention can be found in the subclaims and the detailed description below.

In the 2-oxopyrrole derivatives of the formula I to be used according to the invention, $R^1$, $R^2$ and A have the following meanings:

$R^1$ is aryl or heteroaryl, where these radicals independently of one another may carry one to five of the following groups: hydrogen, halogen, cyano, nitro, hydroxyl, mercapto, thiocyanato, carboxyl, amino, $C_1$–$C_6$-alkyl, $C_1$–$C_6$-cyanoalkyl, $C_2$–$C_6$-alkenyl, $C_1$–$C_6$-alkoxy-$C_2$–$C_6$-alkenyl, $C_3$–$C_6$-alkynyl, $C_1$–$C_6$-alkoxy-$C_3$–$C_6$-alkynyl, $C_3$–$C_6$-alkynyl-$C_1$–$C_6$-alkoxy, $C_3$–$C_7$-cycloalkyl, $C_1$–$C_6$-alkyl-$C_3$–$C_7$-cycloalkyl, $C_1$–$C_6$-alkoxy-$C_3$–$C_7$-cycloalkyl, $C_3$–$C_7$-cycloalkyloxy, $C_3$–$C_7$-cyanocycloalkyloxy, $C_1$–$C_6$-alkyl-$C_3$–$C_7$-cycloalkyloxy, $C_3$–$C_7$-halocycloalkyl, $C_3$–$C_7$-cyanocycloalkyl, $C_3$–$C_7$-halocycloalkyloxy, $C_5$–$C_7$-cycloalkenyl, $C_1$–$C_6$-alkyl-$C_5$–$C_7$-cycloalkenyl, $C_1$–$C_6$-alkoxy-$C_5$–$C_7$-cycloalkenyl, $C_5$–$C_7$-cyanocycloalkenyl, $C_5$–$C_7$-halocycloalkenyl, $C_1$–$C_6$-alkoxy-$C_1$–$C_6$-alkyl, $C_1$–$C_6$-haloalkyl, $C_2$–$C_6$-haloalkenyl, $C_3$–$C_6$-haloalkynyl, $C_2$–$C_6$-cyanoalkenyl, $C_3$–$C_6$-cyanoalkynyl, $C_1$–$C_6$-alkoxy, $C_1$–$C_6$-cyanoalkoxy, $C_1$–$C_6$-haloalkoxy, $C_2$–$C_6$-alkenyloxy, $C_2$–$C_6$-cyanoalkenyloxy, $C_2$–$C_6$-haloalkenyloxy, $C_2$–$C_6$-alkynyloxy, $C_1$–$C_6$-alkylthio, $C_1$–$C_6$-cyanoalkylthio, $C_1$–$C_6$-haloalkylthio, $C_1$–$C_6$-alkoxy-$C_1$–$C_6$-alkylthio, $C_1$–$C_6$-alkoxycarbonyl, $C_1$–$C_6$-alkylcarbonyl, $C_1$–$C_6$-alkylcarboxy-$C_1$–$C_6$-alkyl, $C_1$–$C_6$-alkylcarbonyl-$C_1$–$C_6$-alkyl, $C_1$–$C_6$-alkylcarbonylamino, arylcarbonylamino, arylsulfinyl, arylsulfonyl, heteroarylsulfinyl, heteroarylsulfonyl, aryl-$C_1$–$C_6$-alkyl, aryl-$C_2$–$C_6$-alkenyl, aryl-$C_3$–$C_6$-alkynyl, heteroaryl-$C_1$–$C_6$-alkyl, heteroaryl-$C_2$–$C_6$-alkenyl, heteroaryl-$C_3$–$C_6$-alkynyl, aryl-$C_1$–$C_6$-alkoxy, aryl-$C_2$–$C_6$-alkenyloxy, aryl-$C_3$–$C_6$-alkynyloxy, heteroaryl-$C_1$–$C_6$-alkoxy, heteroaryl-$C_2$–$C_6$-alkenyloxy, heteroaryl-$C_3$–$C_6$-alkynyloxy, $C_1$–$C_6$-alkylsulfinyl, $C_1$–$C_6$-alkylsulfonyl, $C_2$–$C_6$-alkenylsulfinyl, $C_2$–$C_6$-alkenylsulfonyl, $C_1$–$C_6$-alkylamino, di-$C_1$–$C_6$-alkylamino, HC=NOH, $C_1$–$C_6$-alkyl-C=NOH, HC=N—O—$C_1$–$C_6$-alkyl, HC=N—O—$C_1$–$C_6$-alkyl-aryl, $C_1$–$C_6$-alkyl-C=N—O—$C_1$–$C_6$-alkyl, HC=N—O—$C_2$–$C_6$-alkenyl, $C_1$–$C_6$-alkyl-C=N—O—$C_2$–$C_6$-alkenyl, HC=N—O-aryl, $C_1$–$C_6$-alkyl-C=N—O-aryl, aryl, aryloxy, heteroaryl, heteroaryloxy, arylthio, heteroarylthio, where the cyclic substituents for their part may, independently of one another, carry one to five of the following substituents: hydrogen, halogen, cyano, nitro, hydroxyl, mercapto, thiocyanato, carboxyl, amino, $C_1$–$C_6$-alkyl, $C_1$–$C_6$-cyanoalkyl, $C_2$–$C_6$-alkenyl, $C_1$–$C_6$-alkoxy-$C_2$–$C_6$-alkenyl, $C_3$–$C_6$-alkynyl, $C_1$–$C_6$-alkoxy-$C_3$–$C_6$-alkynyl, $C_3$–$C_6$-alkynyl-$C_1$–$C_6$-alkoxy, $C_3$–$C_7$-cycloalkyl, $C_1$–$C_6$-alkyl-$C_3$–$C_7$-cycloalkyl, $C_1$–$C_6$-alkoxy-$C_3$–$C_7$-cycloalkyl, $C_3$–$C_7$-cycloalkyloxy, $C_3$–$C_7$-cyanocycloalkyloxy, $C_1$–$C_6$-alkyl-$C_3$–$C_7$-cycloalkyloxy, $C_3$–$C_7$-halocycloalkyl, $C_3$–$C_7$-cyanocycloalkyl, $C_3$–$C_7$-halocycloalkyloxy, $C_5$–$C_7$-cycloalkenyl, $C_1$–$C_6$-alkyl-$C_5$–$C_7$-cycloalkenyl, $C_1$–$C_6$-alkoxy-$C_5$–$C_7$-cycloalkenyl, $C_5$–$C_7$-cyanocycloalkenyl, $C_5$–$C_7$-halocycloalkenyl, $C_1$–$C_6$-alkoxy-$C_1$–$C_6$-alkyl, $C_1$–$C_6$-haloalkyl, $C_2$–$C_6$-haloalkenyl, $C_3$–$C_6$-haloalkynyl, $C_2$–$C_6$-cyanoalkenyl, $C_3$–$C_6$-cyanoalkynyl, $C_1$–$C_6$-alkoxy, $C_1$–$C_6$-cyanoalkoxy, $C_1$–$C_6$-haloalkoxy, $C_2$–$C_6$-alkenyloxy, $C_2$–$C_6$-cyanoalkenyloxy, $C_2$–$C_6$-haloalkenyloxy, $C_2$–$C_6$-alkynyloxy, $C_1$–$C_6$-alkylthio, $C_1$–$C_6$-cyanoalkylthio, $C_1$–$C_6$-haloalkylthio, $C_1$–$C_6$-alkoxy-$C_1$–$C_6$-alkylthio, $C_1$–$C_6$-alkoxycarbonyl, $C_1$–$C_6$-alkylcarbonyl, $C_1$–$C_6$-alkylcarboxy-$C_1$–$C_6$-alkyl, $C_1$–$C_6$-alkylcarbonyl-$C_1$–$C_6$-alkyl, $C_1$–$C_6$-alkylcarbonylamino, arylcarbonylamino, arylsulfinyl, arylsulfonyl, heteroarylsulfinyl, heteroarylsulfonyl, aryl-$C_1$–$C_6$-alkyl, aryl-$C_2$–$C_6$-alkenyl, aryl-$C_3$–$C_6$-alkynyl, heteroaryl-$C_1$–$C_6$-alkyl, heteroaryl-$C_2$–$C_6$-alkenyl, heteroaryl-$C_3$–$C_6$-alkynyl, aryl-$C_1$–$C_6$-alkoxy, aryl-$C_2$–$C_6$-alkenyloxy, aryl-$C_3$–$C_6$-alkynyloxy, heteroaryl-$C_1$–$C_6$-alkoxy, heteroaryl-$C_2$–$C_6$-alkenyloxy, heteroaryl-$C_3$–$C_6$-alkynyloxy, $C_1$–$C_6$-alkylsulfinyl, $C_1$–$C_6$-alkylsulfonyl, $C_2$–$C_6$-alkenylsulfinyl, $C_2$–$C_6$-alkenylsulfonyl, $C_1$–$C_6$-alkylamino, di-$C_1$–$C_6$-alkylamino, HC=NOH, $C_1$–$C_6$-alkyl-C=NOH, HC=N—O—$C_1$–$C_6$-alkyl, HC=N—O—$C_1$–$C_6$-alkyl-aryl, $C_1$–$C_6$-alkyl-C=N—O-$C_1$–$C_6$-alkyl, HC=N—O—$C_2$–$C_6$-alkenyl, $C_1$–$C_6$-alkyl-C=N—O—$C_2$–$C_6$-alkenyl, HC=N—O-aryl, $C_1$–$C_6$-alkyl-C=N—O-aryl, aryl, aryloxy, heteroaryl, heteroaryloxy, arylthio, heteroarylthio; or where the aryl or heteroaryl radical forms a bicyclic system with a fused-on phenyl ring, a fused-on $C_3$–$C_6$-carbocycle or a 5- or 6-membered heterocycle, where the fused-on ring system may carry one to three of the substituents mentioned above for aryl;

$R^2$ is $C_1$–$C_6$-alkyl or aryl or heteroaryl, where aryl, heteroaryl may carry one to three of the substituents mentioned under $R^1$ for aryl, is $C_3$–$C_7$-cycloalkyl or $C_1$–$C_6$-alkylaryl;

A is $COOR^3$ or $CONR^3R^4$, where $R^3$ and $R^4$ independently of one another are hydrogen, $C_1$–$C_6$-alkyl, $C_2$–$C_6$-alkenyl, $C_3$–$C_7$-cycloalkyl or $C_1$–$C_6$-alkyl-aryl, which may be partially or fully halogenated or may carry one to three substituents selected from the group consisting of $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl.

With respect to the position of the substituent $R^1$, the 2-oxopyrrole derivatives to be used according to the invention can be employed as E or as Z isomers or as mixtures of the two isomers.

Except for the compounds below, the 2-oxopyrrole derivatives of the formula I to be used according to the invention are novel and are in their own right part of the subject matter of the invention:

| $R^1$ | $R^2$ | A |
|---|---|---|
| $C_6H_5$ | $CH_3$ | $COOC_2H_5$ |
| 4-$(CH_3)_2N$—$C_6H_4$ | $CH_3$ | $COOC_2H_5$ |
| 2-$NO_2$—$C_6H_4$ | $CH_3$ | $COOC_2H_5$ |
| 4-$NO_2$—$C_6H_4$ | $CH_3$ | $COOC_2H_5$ |
| 4-Cl—$C_6H_4$ | $CH_3$ | $COOC_2H_5$ |
| 4-Br—$C_6H_4$ | $CH_3$ | $COOC_2H_5$ |
| 4-$CH_3$—$C_6H_4$ | $CH_3$ | $COOC_2H_5$ |
| 4-HO—$C_6H_4$ | $CH_3$ | $COOC_2H_5$ |
| 2,4-$(CH_3)_2$-5-$COOCH_2CH_3$-pyrrol-3-yl | $CH_3$ | $COOC_2H_5$ |
| 3,5-$(CH_3)_2$-4-$COOCH_2CH_3$-pyrrol-2-yl | $CH_3$ | $COOC_2H_5$ |
| $C_6H_5$ | $C_6H_5$ | $COOCH_3$ |
| 2-$COOCH_2CH_3$-5-$CH_3O$-indol-3-yl | $CH_3$ | $COOC_2H_5$ |
| 4-$CH_3O$—$C_6H_4$ | $CH_3$ | $COOC_2H_5$ |

The organic molecular moieties mentioned in the definitions of $R^1$, $R^2$ and A are collective terms for individual enumerations of the individual meanings. All carbon chains, i.e. all alkyl, haloalkyl, cyanoalkyl, alkoxy, haloalkoxy, cyanoalkoxy, alkylthio, alkylsulfinyl, alkylsulfonyl, alkylamino, dialkylamino, alkyloximino, alkyliminooxy, alkenyl, alkenyloxy, alkynyl, alkynyloxy and alkynylthio moieties may be straight-chain or branched. Halogenated substituents preferably carry one to five identical or different halogen atoms.

The term "halogen" in each case means fluorine, bromine, chlorine or iodine, in particular fluorine or chlorine.

Examples of other meanings are:

$C_1$–$C_6$-alkyl: methyl, ethyl, n-propyl, 1-methylethyl, n-butyl, 1-methylpropyl, 2-methylpropyl or 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular methyl, ethyl, n-propyl, 1-methylethyl, n-butyl, 1,1-dimethylethyl, n-pentyl or n-hexyl;

$C_1$–$C_6$-haloalkyl: $C_1$–$C_6$-alkyl as mentioned above which is partially or fully substituted by fluorine, chlorine, bromine and/or iodine, i.e., for example, one of the radicals mentioned under $C_1$–$C_4$-haloalkyl, or 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl, in particular chloromethyl, fluoromethyl, difluoromethyl, trifluoromethyl, 2-fluoroethyl, 2-chloroethyl or 2,2,2-trifluoroethyl;

$C_1$–$C_6$-alkylamino: methylamino, ethylamino, n-propylamino, 1-methylethylamino, n-butylamino, 1-methylpropylamino, 2-methylpropylamino, 1,1-dimethylethylamino, n-pentylamino, 1-methylbutylamino, 2-methylbutylamino, 3-methylbutylamino, 2,2-dimethylpropylamino, 1-ethylpropylamino, n-hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino, in particular methylamino, ethylamino, n-propylamino, 1-methylethylamino, n-butylamino, 1,1-dimethylethylamino, n-pentylamino or n-hexylamino;

cyano-$C_1$–$C_6$-alkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl or 2-cyanomethylprop-2-yl, in particular cyanomethyl or 2-cyanoethyl;

($C_1$–$C_6$-alkyl)carbonyl: methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, in particular methylcarbonyl, ethylcarbonyl or 1-methylethylcarbonyl;

($C_1$–$C_6$-alkyl)carbonyl-$C_1$–$C_6$-alkyl: $C_1$–$C_6$-alkyl which is substituted by ($C_1$–$C_6$-alkyl)carbonyl as mentioned above, i.e., for example, methylcarbonylmethyl;

($C_1$–$C_6$-alkyl)carboxyl: $C_1$–$C_6$-alkyl as defined above which is substituted by a carboxyl group, for example methylcarboxyl, ethylcarboxyl, n-propylcarboxyl, 1-methylethylcarboxyl, n-butylcarboxyl, 1-methylpropylcarboxyl, 2-methylpropylcarboxyl or 1,1-dimethylethylcarboxyl, in particular methylcarboxyl;

($C_1$–$C_6$-alkylcarboxyl)-$C_1$–$C_6$-alkyl: $C_1$–$C_6$-alkylcarboxyl as mentioned above which is substituted by a $C_1$–$C_6$-alkyl group as defined above;

$C_1$–$C_6$-alkoxy: methoxy, ethoxy, n-propoxy, 1-methylethoxy, n-butoxy, 1-methylpropoxy, 2-methylpropoxy or 1,1-dimethylethoxy, e.g. n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, in particular methoxy, ethoxy or 1-methylethoxy;

$C_1$–$C_6$-haloalkoxy: a $C_1$–$C_6$-alkoxy radical as mentioned above which is partially or fully substituted by fluorine, chlorine, bromine and/or iodine, i.e., for example, one of the radicals mentioned under $C_1$–$C_4$-haloalkoxy, or 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, in particular chloromethoxy, fluoromethoxy, difluoromethoxy, trifluoromethoxy, 2-fluoroethoxy, 2-chloroethoxy or 2,2,2-trifluoroethoxy;

($C_1$–$C_6$-alkoxy)carbonyl: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl or 1,1-dimethylethoxycarbonyl, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, in particular methoxycarbonyl, ethoxycarbonyl or 1-methylethoxycarbonyl;

$C_1$–$C_6$-alkylthio: methylthio, ethylthio, n-propylthio, 1-methylethylthio, n-butylthio, 1-methylpropylthio, 2-methylpropylthio, 1,1-dimethylethylthio, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, in particular methylthio or ethylthio;

$C_1$–$C_6$-haloalkylthio: $C_1$–$C_6$-alkylthio as mentioned above which is partially or fully substituted by fluorine, chlorine and/or bromine, i.e., for example, one of the radicals mentioned under $C_1$–$C_4$-haloalkylthio, or 5-fluoropentylthio, 5-chloropentylthio, 5-bromopentylthio, 5-iodopentylthio, undecafluoropentylthio, 6-fluorohexylthio or 6-chlorohexylthio, in particular chloromethylthio, fluoromethylthio, difluoromethylthio, trifluoromethylthio, 2-fluoroethylthio, 2-chloroethylthio or 2,2,2-trifluoroethylthio;

$C_1$–$C_6$-alkylsulfinyl: methylsulfinyl, ethylsulfinyl, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl, in particular methylsulfinyl;

$C_1$–$C_6$-alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, in particular methylsulfonyl;

$C_2$–$C_6$-alkenyl: for example ethenyl, prop-2-en-1-yl, n-buten-4-yl, 1-methylprop-2-en-1-yl, 2-methylprop-2-en-1-yl, 2-buten-1-yl, n-penten-3-yl, n-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, n-hex-3-en-1-yl, n-hex-4-en-1-yl, n-hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl, in particular ethenyl, prop-2-en-1-yl or n-buten-4-yl;

$C_2$–$C_6$-alkenylsulfinyl: $C_2$–$C_6$-alkenyl as defined above which is substituted by a sulfinyl group, for example ethenylsulfinyl, prop-2-en-1-ylsulfinyl, n-buten-4-ylsulfinyl, 1-methylprop-2-en-1-ylsulfinyl, 2-methylprop-2-en-1-ylsulfinyl, 2-buten-1-ylsulfinyl, n-penten-3-ylsulfinyl, n-penten-4-ylsulfinyl, 1-methylbut-2-en-1-ylsulfinyl, 2-methylbut-2-en-1-ylsulfinyl, 3-methylbut-2-en-1-ylsulfinyl, 1-methylbut-3-en-1-ylsulfinyl, 2-methylbut-3-en-1-ylsulfinyl, 3-methylbut-3-en-1-ylsulfinyl, 1,1-dimethylprop-2-en-1-ylsulfinyl, 1,2-dimethylprop-2-en-1-ylsulfinyl, 1-ethylprop-2-en-1-ylsulfinyl, n-hex-3-en-1-ylsulfinyl, n-hex-4-en-1-ylsulfinyl, n-hex-5-en-1-ylsulfinyl, 1-methylpent-3-en-1-ylsulfinyl, 2-methylpent-3-en-1-ylsulfinyl, 3-methylpent-3-en-1-ylsulfinyl, 4-methylpent-3-en-1-ylsulfinyl, 1-methylpent-4-en-1-ylsulfinyl, 2-methylpent-4-en-1-ylsulfinyl, 3-methylpent-4-en-1-ylsulfinyl, 4-methylpent-4-en-1-ylsulfinyl, 1,1-dimethylbut-2-en-1-yl, 1,1-dimethylbut-3-en-1-ylsulfinyl, 1,2-dimethylbut-2-en-1-ylsulfinyl, 1,2-dimethylbut-3-en-1-ylsulfinyl, 1,3-dimethylbut-2-en-1-ylsulfinyl, 1,3-dimethylbut-3-en-1-ylsulfinyl, 2,2-dimethylbut-3-en-1-ylsulfinyl, 2,3-dimethylbut-2-en-1-ylsulfinyl, 2,3-dimethylbut-3-en-1-ylsulfinyl, 3,3-dimethylbut-2-en-1-ylsulfinyl, 1-ethylbut-2-en-1-ylsulfinyl, 1-ethylbut-3-en-1-ylsulfinyl, 2-ethylbut-2-en-1-ylsulfinyl, 2-ethylbut-3-en-1-ylsulfinyl, 1,1,2-trimethylprop-2-en-1-ylsulfinyl, 1-ethyl-1-methylprop-2-en-1-ylsulfinyl or 1-ethyl-2-methylprop-2-en-1-ylsulfinyl, in particular ethenylsulfinyl, prop-2-en-1-ylsulfinyl or n-buten-4-ylsulfinyl;

$C_2$–$C_6$-alkenylsulfonyl: $C_2$–$C_6$-alkenyl as defined above which is substituted by a sulfonyl group, for example ethenylsulfonyl, prop-2-en-1-ylsulfonyl, n-buten-4-ylsulfonyl, 1-methylprop-2-en-1-ylsulfonyl, 2-methylprop-2-en-1-ylsulfonyl, 2-buten-1-ylsulfonyl, n-penten-3-ylsulfonyl, n-penten-4-ylsulfonyl, 1-methylbut-2-en-1-ylsulfonyl, 2-methylbut-2-en-1-ylsulfonyl, 3-methylbut-2-en-1-ylsulfonyl, 1-methylbut-3-en-1-ylsulfonyl, 2-methylbut-3-en-1-ylsulfonyl, 3-methylbut-3-en-1-ylsulfonyl, 1,1-dimethylprop-2-en-1-ylsulfonyl, 1,2-dimethylprop-2-en-1-ylsulfonyl, 1-ethylprop-2-en-1-ylsulfonyl, n-hex-3-en-1-ylsulfonyl, n-hex-4-en-1-ylsulfonyl, n-hex-5-en-1-ylsulfonyl, 1-methylpent-3-en-1-ylsulfonyl, 2-methylpent-3-en-1-ylsulfonyl, 3-methylpent-3-en-1-ylsulfonyl, 4-methylpent-3-en-1-ylsulfonyl, 1-methylpent-4-en-1-ylsulfonyl, 2-methylpent-4-en-1-ylsulfonyl, 3-methylpent-4-en-1-ylsulfonyl, 4-methylpent-4-en-1-ylsulfonyl, 1,1-dimethylbut-2-en-1-yl, 1,1-dimethylbut-3-en-1-ylsulfonyl, 1,2-dimethylbut-2-en-1-ylsulfonyl, 1,2-dimethylbut-3-en-1-ylsulfonyl, 1,3-dimethylbut-2-en-1-ylsulfonyl, 1,3-dimethylbut-3-en-1-ylsulfonyl, 2,2-dimethylbut-3-en-1-ylsulfonyl, 2,3-dimethylbut-2-en-1-ylsulfonyl, 2,3-dimethylbut-3-en-1-ylsulfonyl, 3,3-dimethylbut-2-en-1-ylsulfonyl, 1-ethylbut-2-en-1-ylsulfonyl, 1-ethylbut-3-en-1-ylsulfonyl, 2-ethylbut-2-en-1-ylsulfonyl, 2-ethylbut-3-en-1-ylsulfonyl, 1,1,2-trimethylprop-2-en-1-ylsulfonyl, 1-ethyl-1-methylprop-2-en-1-ylsulfonyl or 1-ethyl-2-methylprop-2-en-1-ylsulfonyl, in particular ethenylsulfonyl, prop-2-en-1-ylsulfonyl or n-buten-4-ylsulfonyl;

$C_2$–$C_6$-haloalkenyl: $C_2$–$C_6$-alkenyl as mentioned above which is partially or fully substituted by fluorine, chlorine and/or bromine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl, in particular 2-chloroallyl or 3,3-dichloroallyl;

$C_2$–$C_6$-alkenyloxy: ethenyloxy, prop-1-en-1-yloxy, prop-2-en-1-yloxy, 1-methylethenyloxy, n-buten-1-yloxy, n-buten-2-yloxy, n-buten-3-yloxy, 1-methylprop-1-en-1-yloxy, 2-methylprop-1-en-1-yloxy, 1-methylprop-2-en-1-yloxy, 2-methylprop-2-en-1-yloxy, n-penten-1-yloxy, n-penten-2-yloxy, n-penten-3-yloxy, n-penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, n-hex-1-en-1-yloxy, n-hex-2-en-1-yloxy, n-hex-3-en-1-yloxy, n-hex-4-en-1-yloxy, n-hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy or 1-ethyl-2-methylprop-2-en-1-yloxy, in particular ethenyloxy or prop-2-en-1-yloxy;

$C_3$–$C_6$-alkinyl: ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, in particular ethynyl or prop-2-yn-1-yl;

$C_2$–$C_6$-alkynyloxy: ethynyloxy, prop-1-yn-1-yloxy, prop-2-yn-1-yloxy, n-but-1-yn-1-yloxy, n-but-1-yn-3-yloxy, n-but-1-yn-4-yloxy, n-but-2-yn-1-yloxy, n-pent-1-yn-1-yloxy, n-pent-1-yn-3-yloxy, n-pent-1-yn-4-yloxy, n-pent-1-yn-5-yloxy, n-pent-2-yn-1-yloxy, n-pent-2-yn-4-yloxy, n-pent-2-yn-5-yloxy, 3-methylbut-1-yn-3-yloxy, 3-methylbut-1-yn-4-yloxy, n-hex-1-yn-1-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-1-yloxy, 3-methylpent-1-yn-3-yloxy, 3-methylpent-1-yn-4-yloxy, 3-methylpent-1-yn- 5-yloxy, 4-methylpent-1-yn-1-yloxy, 4-methylpent-2-yn-4-yloxy or 4-methylpent-2-yn-5-yloxy, in particular ethynyloxy or prop-2-yn-1-yloxy;

$C_3$–$C_7$-cycloalkyl: cyclopropyl, cyclobutyl, cyclopentyl, cyclohexyl or cycloheptyl, in particular cyclopentyl or cyclohexyl;

A preferred process variant is shown in the reaction scheme 1 below. The specific reaction conditions are known to the person skilled in the art:

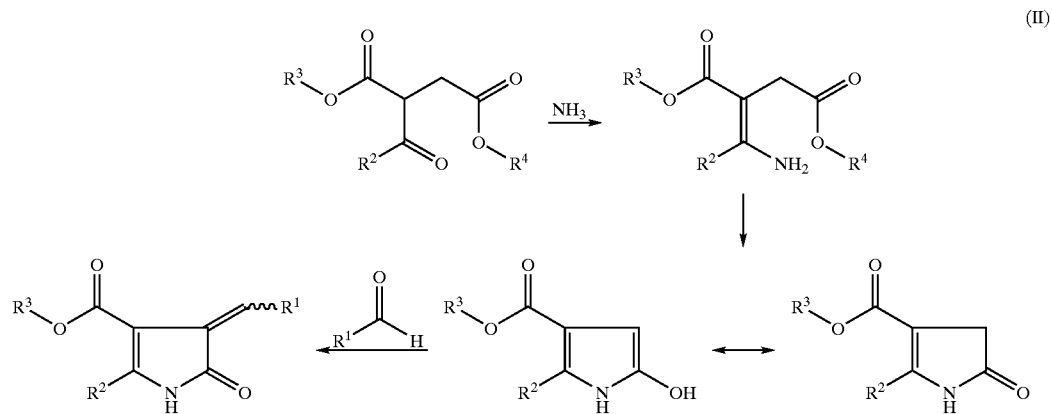

(II)

$C_3$–$C_7$-cycloalkyloxy: cyclopropyloxy, cyclobutyloxy, cyclopentyloxy, cyclohexyloxy or cycloheptyloxy;

$C_5$–$C_7$-cycloalkenyl: cyclopent-1-enyl, cyclopent-2-enyl, cylopent-3-enyl, cyclohex-1-enyl, cyclohex-2-enyl, cyclohex-3-enyl, cyclohept-1-enyl, cyclohept-2-enyl, cyclohept-3-enyl or cyclohept-4-enyl;

heteroaryl: aromatic heterocycles having one to three heteroatoms selected from a group consisting of
one to three nitrogen atoms
one or two oxygen atoms and
one or two sulfur atoms, for example furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl, such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridyl, such as 2-pyridyl, 3-pyridyl and 4-pyridyl, pyridazinyl, such as 3-pyridazinyl and 4-pyridazinyl, pyrimidinyl, such as 2-pyrimidinyl, 4-pyrimidinyl and 5-pyrimidinyl, furthermore 2-pyrazinyl, 1,3,5-triazin-2-yl and 1,2,4-triazin-3-yl, in particular pyridyl, pyrimidyl, furanyl and thienyl;

Aryl: $C_6$–$C_{14}$-aryl, such as phenyl, naphthyl, anthracenyl, preferably phenyl.

The 2-oxopyrrole derivatives can be obtained by processes known per se to the person skilled in the art and described in the literature, so that further details do not have to be given here. Only by way of example, reference is made to the processes described in Z. Physiol. Chem. 132 (1924), 72 and J. Org. Chem. 57, (1992), 6032.

A further synthesis is possible analogously to processes known per se via the intermediates of the formulae IIa, IIb and IIc, which also form part of the subject matter of the invention.

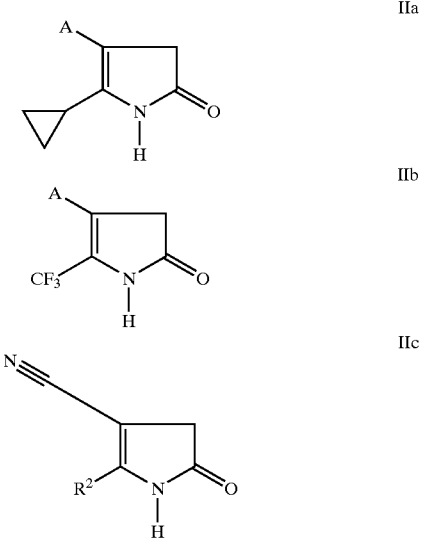

IIa

IIb

IIc

Synthesis of Methyl 2-trifluoromethyl-5-oxo-4,5-dihydropyrrole-3-carboxylate (IIb)

2 g (8.2 mmol) of dimethyl trifluoroacetylbutanedicarboxylate were dissolved in 100 ml of methanol and, at 0–5° C., saturated with ammonia gas. The mixture was then stirred at room temperature for 12 h and concentrated and the residue was taken up in 50 ml of xylene, and, after addition of a spatula tip of p-toluenesulfonic acid, refluxed for 6 h.

The mixture was filtered and the resulting filtrate was diluted with water and extracted with ethyl acetate. The organic phase was then concentrated and dried. (MH+210).

Synthesis of 2-methyl-5-oxo-4,5-dihydropyrrole-3-carbonitrile IIc

A mixture of 0.9 g (4.6 mmol) of 2-methyl-5-oxo-4,5-dihydropyrrole-3-carboxamide, 1.4 g (9.2 mmol) of phosphorus oxychloride and 0.9 g (6.4 mmol) of potassium carbonate in 50 ml of acetone was refluxed for 6 h. The mixture was then concentrated and the resulting residue was chromatographed over silica gel (mobile phase: cyclohexane:ethyl acetate 10:1 to 1:1). This gave 0.15 g (19% of theory) of the desired product (IR: 2220 $cm^{-1}$).

According to the invention, preference is given to using 2-oxopyrrole derivatives in which $R^2$ is a $C_1$–$C_6$-alkyl group, A is a grouping COO—$C_1$–$C_6$-alkyl and $R^1$ has the meanings given in Tables A and B below.

Particular preference is given to the compounds of the formula I in which $R^2$ is methyl, ethyl or propyl and A is $COOCH_3$ or $COOC_2H_5$ and $R^1$ has one of the meanings given in Tables A and B below for aryl or heteroaryl. Very particular preference is given to compounds in which $R^2$ is methyl and A is $COOCH_3$ and $R^1$ is an aryl radical which is substituted in the 2 or 2,6 position and which may be substituted by one or more halogen, alkyl or haloalkyl groups.

Preference is furthermore given to compounds in which $R^1$ is a heteroaromatic radical, in particular a substituted pyrazole radical which may carry one or more halogen substituents.

TABLE A

| No. | $R^1$ = aryl Meaning of $R^1$ |
|---|---|
| A.1. | $C_6H_5$ |
| A.2. | 4-$CCl_3$—$C_6H_4$ |
| A.3. | 1-naphthyl |
| A.4. | 2-naphthyl |
| A.5. | 2-$CH_3$—$C_6H_4$ |
| A.6. | 3-$CH_3$—$C_6H_4$ |
| A.7. | 4-$CH_3$—$C_6H_4$ |
| A.8. | 3,5-$(CH_3)_2$—$C_6H_3$ |
| A.9. | 2,4-$(CH_3)_2$—$C_6H_3$ |
| A.10. | 3,4-$(CH_3)_2$—$C_6H_3$ |
| A.11. | 2,4,6-$(CH_3)_3$—$C_6H_2$ |
| A.12. | 2-$C_2H_5$—$C_6H_4$ |
| A.13. | 4-$C_2H_5$—$C_6H_4$ |
| A.14. | 4-$(C_2H_5)C(CH_3)_2$—$C_6H_4$ |
| A.15. | 2-$CH_3$-4-$C_4H_9$—$C_6H_3$ |
| A.16. | 2-$CH_3$-4-$CH_3O$—$C_6H_3$ |
| A.17. | 2-$CH_3$-4-$C_6H_5$—$C_6H_3$ |
| A.18. | 3,5-$(Cl)_2$-4-$CH_3$-$C_6H_2$ |
| A.19. | 4-t-$C_4H_9$—$C_6H_4$ |
| A.20. | 4-$(CH_3)_2CH$—$C_6H_4$ |
| A.21. | 4-$CH_2$=$C(CH_3)$—$C_6H_4$ |
| A.22. | 3-t-$C_4H_9$-4-$CH_3$—$C_6H_3$ |
| A.23. | 2-$CH_3$-3-$C_4H_9$—$C_6H_3$ |
| A.24. | 2,5-$(CH_3)_2$-4-$CH_3O$—$C_6H_2$ |
| A.25. | 2-Cl—$C_6H_4$ |
| A.26. | 4-Cl—$C_6H_4$ |
| A.27. | 3-Cl—$C_6H_4$ |
| A.28. | 3,5-$(Cl)_2$—$C_6H_3$ |
| A.29. | 2,4-$(Cl)_2$—$C_6H_3$ |
| A.30. | 2,3-$(Cl)_2$—$C_6H_3$ |
| A.31. | 3,4-$(Cl)_2$—$C_6H_3$ |
| A.32. | 2-Cl-4-F-$C_6H_3$ |
| A.33. | 2-Cl-6-F-$C_6H_3$ |
| A.34. | 2-Cl-5-$NO_2$—$C_6H_3$ |
| A.35. | 3-Cl-6-$NO_2$—$C_6H_3$ |
| A.36. | 2-Br—$C_6H_4$ |
| A.37. | 3-Br—$C_6H_4$ |
| A.38. | 4-Br—$C_6H_4$ |
| A.39. | 4-$CF_2Cl$—$C_6H_4$ |

TABLE A-continued

| No. | $R^1$ = aryl Meaning of $R^1$ |
|---|---|
| A.40. | 2-$CF_3$—$C_6H_4$ |
| A.41. | 4-$CF_3$—$C_6H_4$ |
| A.42. | 2,5-$(CF_3)_2$—$C_6H_3$ |
| A.43. | 4-$CH_3O$—$C_6H_4$ |
| A.44. | 2-$CH_3O$—$C_6H_4$ |
| A.45. | 2,4-$(CH_3O)_2$—$C_6H_3$ |
| A.46. | 2,5-$(CH_3O)_2$—$C_6H_3$ |
| A.47. | 3,5- $(CH_3O)$ 2-$C_6H_3$ |
| A.48. | 2,4,6-$(CH_3O)_3$—$C_6H_2$ |
| A.49. | 2,3,4-$(CH_3O)_3$—$C_6H_2$ |
| A.50. | 3,4,5-$(CH_3O)_3$—$C_6H_2$ |
| A.51. | 2,4,5-$(CH_3O)_3$—$C_6H_2$ |
| A.52. | 3-Br-4,5-$(CH_3O)_2$—$C_6H_2$ |
| A.53. | 4-$C_2H_5O$—$C_6H_4$ |
| A.54. | 3-$C_2H_5O$—$C_6H_4$ |
| A.55. | 2-$C_2H_5O$—$C_6H_4$ |
| A.56. | 4-$C_3H_7O$—$C_6H_4$ |
| A.57. | 4-$C_6H_{13}O$—$C_6H_4$ |
| A.58. | 3-$C_6H_5O$—$C_6H_4$ |
| A.59. | 4-$CH_3S$—$C_6H_4$ |
| A.60. | 2-OH—$C_6H_4$ |
| A.61. | 4-OH—$C_6H_4$ |
| A.62. | 2-OH-5-Br—$C_6H_3$ |
| A.63. | 2,3-$(OH)_2$—$C_6H_3$ |
| A.64. | 3,4-$(OH)_2$—$C_6H_3$ |
| A.65. | 2-OH-3-$CH_3O$—$C_6H_3$ |
| A.66. | 2-OH-5-$CH_3O$—$C_6H_3$ |
| A.67. | 3-OH-4-$CH_3O$—$C_6H_3$ |
| A.68. | 3-OH-4-$C_2H_5O$—$C_6H_3$ |
| A.69. | 3-$C_2H_5O$-4-$CH_3O$—$C_6H_3$ |
| A.70. | 2-$CH_3O$-5-Br—$C_6H_3$ |
| A.71. | 2,3-$(CH_3)_2$-4-$CH_3O$—$C_6H_2$ |
| A.72. | 3-Br-4-$CH_3O$—$C_6H_3$ |
| A.73. | 3-$CH_3O$-4-OH-5-Br—$C_6H_2$ |
| A.74. | 2-OH-5-Cl—$C_6H_3$ |
| A.75. | 2-OH-3-$NO_2$—$C_6H_3$ |
| A.76. | 2-$NO_2$-4,5-$(CH_3O)_2$—$C_6H_2$ |
| A.77. | 4-n-$C_4H_9$—$C_6H_4$ |
| A.78. | 4-$CH_2$=CH—$CH_2O$—$C_6H_4$ |
| A.79. | 2-F-$C_6H_4$ |
| A.80. | 3-F-$C_6H_4$ |
| A.81. | 4-F-$C_6H_4$ |
| A.82. | 2,4-$F_2$—$C_6H_4$ |
| A.83. | 2,6-$F_2$—$C_6H_4$ |
| A.84. | 2-F-5-$NO_2$—$C_6H_3$ |
| A.85. | 3-F-6-$NO_2$—$C_6H_3$ |
| A.86. | 2-Br-4-F—$C_6H_3$ |
| A.87. | 4-CN—$C_6H_4$ |
| A.88. | 2-CN—$C_6H_4$ |
| A.89. | 3-CN—$C_6H_4$ |
| A.90. | 2-$NO_2$—$C_6H_4$ |
| A.91. | 3-$NO_2$—$C_6H_4$ |
| A.92. | 4-$NO_2$—$C_6H_4$ |
| A.93. | 4-COOH—$C_6H_4$ |
| A.94. | 2-OH-3-$NO_2$—$C_6H_3$ |
| A.95. | 3,4-$(CH_3)_2$-6-Br—$C_6H_2$ |
| A.96. | 3-$CH_3$-4-$CH_3O$—$C_6H_3$ |
| A.97. | 3-$NO_2$-4-Cl—$C_6H_3$ |
| A.98. | 4-$C_6H_4O$—$C_6H_4$ |
| A.99. | 4-Cl-$C_6H_4$—$C_6H_4$ |
| A.100. | 4-(2,3-$Cl_2$—$C_6H_3O$)—$C_6H_4$ |
| A.101. | 4-(3,4-$Cl_2$—$C_6H_3O$)—$C_6H_4$ |
| A.102. | 4-(3-$C_2H_5$—$C_6H_3O$)—$C_6H_4$ |
| A.103. | 4-(4-$C_2H_5$—$C_6H_3O$)—$C_6H_4$ |
| A.104. | 4-(4-Cl-$C_6H_3O$)—$C_6H_4$ |
| A.105. | 4-(4-Br-$C_6H_3O$)—$C_6H_4$ |
| A.106. | 4-(2-Cl-5-$CH_3$—$C_6H_3O$)—$C_6H_4$ |
| A.107. | 4-(2,5-$Cl_2$—$C_6H_3O$)—$C_6H_4$ |
| A.108. | 4-(2-Cl-$C_6H_3O$)—$C_6H_4$ |
| A.109. | 4-(2-F-$C_6H_3O$)—$C_6H_4$ |
| A.110. | 4-(2-Br-$C_6H_3O$)—$C_6H_4$ |
| A.111. | 4-(3,5-$Cl_2$—$C_6H_3O$)—$C_6H_4$ |
| A.112. | 4-(3-$CF_3$—$C_6H_3O$)—$C_6H_4$ |
| A.113. | 4-(3-Cl—$C_6H_3O$)—$C_6H_4$ |
| A.114. | 4-(3-Br—$C_6H_3O$)—$C_6H_4$ |

TABLE A-continued

R¹ = aryl

| No. | Meaning of R¹ |
|---|---|
| A.115. | 4-(4-CH$_3$O—C$_6$H$_4$O)—C$_6$H$_4$ |
| A.116. | 2-Cl-4-NO$_2$—C$_6$H$_3$ |
| A.117. | 3-Br-4-CH$_3$O—C$_6$H$_3$ |
| A.118. | 3-(CH$_3$)$_2$N—C$_6$H$_4$ |
| A.119. | 4-(C$_2$H$_5$)$_2$N—C$_6$H$_4$ |
| A.120. | 4-CH$_2$=CH—C$_6$H$_4$ |
| A.121. | 2-NO$_2$-4-(CH$_3$)$_2$N—C$_6$H$_3$ |
| A.122. | 2-(2-Cl-C$_6$H$_4$)CH$_2$O-C$_6$H$_4$ |
| A.123. | 2-(2-CH$_3$—C$_6$H$_4$)CH$_2$O-C$_6$H$_4$ |
| A.124. | 2-(3-CH$_3$—C$_6$H$_4$)CH$_2$O-C$_6$H$_4$ |
| A.125. | 2-C$_6$H$_4$—CH$_2$O—C$_6$H$_4$ |
| A.126. | 4-C$_6$H$_4$—CH$_2$O—C$_6$H$_4$ |
| A.127. | 4-(COOC$_2$H$_5$)—C$_6$H$_4$ |
| A.128. | 2-NO$_2$-4-(2-Br-4-CF$_3$—C$_6$H$_3$O)—C$_6$H$_3$ |
| A.129. | 3,5-I$_2$-4-OH—C$_6$H$_2$ |
| A.130. | 2-CH$_3$O-5-COOCH$_3$—C$_6$H$_3$ |
| A.131. | 2-OH-4-(C$_2$H$_5$)N—C$_6$H$_3$ |
| A.132. | 3-CH$_3$O-4-OCOCH$_3$—C$_6$H$_3$ |
| A.133. | 3,5,-I$_2$-2-OH—C$_6$H$_2$ |
| A.134. | 2-(Cyclohexyl-2-en)—C$_6$H$_4$ |
| A.135. | 3-C$_6$H$_4$—CH$_2$—O—C$_6$H$_4$ |
| A.136. | 2-NH$_2$-5-NO$_2$—C$_6$H$_3$ |
| A.137. | 2-(4-Cl—C$_6$H$_4$)S—C$_6$H$_4$ |
| A.138. | 3-CH$_3$COOCH$_2$—C$_6$H$_4$ |
| A.139. | 4-CH$_3$O-3-(C$_6$H$_5$)CH$_2$O—C$_6$H$_3$ |
| A.140. | 3-CH$_3$O-2-(C$_6$H$_5$)CH$_2$O—C$_6$H$_3$ |
| A.141. | 3-CH$_3$O-2-(C$_6$H$_5$)CH$_2$O-4-OH—C$_6$H$_2$ |
| A.142. | 2-OH-3,5-Br$_2$—C$_6$H$_2$ |
| A.143. | 3-CH$_3$O-4-(C$_6$H$_4$)CH$_2$O—C$_6$H$_3$ |
| A.144. | 2-CH$_3$O-naphthyl |
| A.145. | 4-NH$_2$—C$_6$H$_4$ |
| A.146. | 4-CH$_3$O-3-(3-CH$_3$—C$_6$H$_4$)CH$_2$O—C$_6$H$_3$ |
| A.147. | 2-OH-3-C$_6$H$_5$—C$_6$H$_3$ |
| A.148. | 4-CH$_3$CONH—C$_6$H$_4$ |
| A.149. | 4-CH$_3$ON=C—C$_6$H$_4$ |
| A.150. | 4-C$_6$H$_5$—C$_6$H$_4$ |
| A.151. | 4-CH≡C—CH$_2$O—C$_6$H$_4$ |
| A.152. | 4-CH$_3$SO—C$_6$H$_4$ |
| A.153. | 2-SO$_3$H-4-Cl—C$_6$H$_3$ |
| A.154. | 4-N≡C—CH$_2$O—C$_6$H$_4$ |
| A.155. | 3-(5-pyrimidyl)—C$_6$H$_4$ |
| A.156. | 3,5-di-C$_4$H$_9$-4-OH—C$_6$H$_2$ |
| A.157. | 4-t-C$_4$H$_9$O—C$_6$H$_4$ |
| A.158. | 1,1,2,3,3-penta-CH$_3$-indan-5-yl |
| A.159. | 4-(2-CN—C$_6$H$_4$—CH=CH)—C$_6$H$_4$ |
| A.160. | 2-N-phthalimid-C$_6$H$_4$ |
| A.161. | 2-NH$_2$—C$_6$H$_4$ |
| A.162. | 4-((ClCH$_2$CH$_2$)(CH$_3$CH$_2$)N)—C$_6$H$_4$ |
| A.163. | 4-CH$_3$OCOO-C$_6$H$_4$ |
| A.164. | 2-NH$_2$-5-NO$_2$—C$_6$H$_3$ |
| A.165. | 2-N-phahalimid-5-NO—C$_6$H$_3$ |
| A.166. | 3,5-di-CH$_3$OCO-4-OH—C$_6$H$_2$ |
| A.167. | 2-OH-5-(CH2=CHCONCH$_2$)—C$_6$H$_3$ |
| A.168. | 4-CH$_3$O-3-(CH2=CHCONCH$_2$)—C$_6$H$_3$ |
| A.169. | 3-N(CH$_3$)$_2$—C$_6$H$_4$ |
| A.170. | 2-(CH$_3$COOCH$_2$)-4-(N(CH$_3$)$_2$)—C$_6$H$_3$ |
| A.171. | 4-(CH$_3$O—C(CH$_3$)$_2$)C—C$_6$H$_4$ |
| A.172. | 2-COOH—C$_6$H$_4$ |
| A.173. | 4-(((CH$_3$)$_2$-N—CH$_2$—CH$_2$—N(CH$_3$)$_2$—C$_6$H$_4$ |
| A.174. | 2-NO$_2$-4-N(CH$_3$)$_2$—C$_6$H$_3$ |
| A.175. | 2-COOH-4-N(CH$_3$)$_2$—C$_6$H$_3$ |
| A.176. | 2-C$_6$H$_5$CH$_2$S-4-N(CH$_3$)$_2$—C$_6$H$_3$ |
| A.177. | ((4-CNC$_6$H$_4$—CH$_2$—CH$_2$—N(CH$_3$))—C$_6$H$_4$ |
| A.178. | 4-ClCH$_2$—C$_6$H$_4$ |
| A.179. | 2-CH$_3$-4-t-C$_4$H$_9$—C$_6$H$_3$ |
| A.180. | 3-t-C$_4$H$_9$-4-CH$_3$O—C$_6$H$_3$ |
| A.181. | 4-(CH$_3$)$_2$C(OH)—C$_6$H$_4$ |
| A.182. | 4-(t-C$_4$H$_9$—COO)—C$_6$H$_4$ |
| A.183. | 3,5-di-t-C$_4$H$_9$-4-CH$_3$O-C$_6$H$_2$ |
| A.184. | 4-CH$_3$CH$_2$O—C(CH$_3$)CH$_2$—C$_6$H$_4$ |
| A.185. | 3,5-di-CH$_3$-4-OH—C$_6$H$_2$ |
| A.186. | 3-(CH$_2$=C(CH$_3$)CONHCH$_2$)-6-OH—C$_6$H$_3$ |
| A.187. | 3,5-di-t-C$_4$H$_9$-4-OH—C$_6$H$_2$ |
| A.188. | 4-CH$_3$CH2C(CH$_3$)$_2$—C$_6$H$_4$ |
| A.189. | 2-CH$_3$-4-CH$_3$CH$_2$C(CH$_3$)$_3$—C$_6$H$_3$ |
| A.190. | 2-CH$_3$-4-CH$_3$O—C$_6$H$_3$ |
| A.191. | 1,1,3,4,4-penta-CH$_3$-tetralin-6-yl |
| A.192. | 1,1,3-tri-CH$_3$-3-((CH$_3$)$_3$CCH$_2$)-indan-5-yl |
| A.193. | 1,1,3-tri-CH$_3$-4-((CH$_3$)$_3$CCH$_2$)-indan-5-yl |
| A.194. | 2-CH$_3$S—C$_6$H$_4$ |
| A.195. | 2-CF$_3$S—C$_6$H$_4$ |
| A.196. | 3-CF$_3$S—C$_6$H$_4$ |
| A.197. | 4-CF$_3$S—C$_6$H$_4$ |
| A.198. | 4-CH$_3$SO$_2$—C$_6$H$_4$ |
| A.199. | 2-Cl-4-CH$_3$SO$_2$—C$_6$H$_3$ |
| A.200. | 4-(C$_6$H$_5$—C≡C)—C$_6$H$_4$ |
| A.201. | 4-(2-CN-thiophen-3-yl)-CH$_2$—O—C$_6$H$_4$ |
| A.202. | 4-(CH$_3$OCO—CH=CH)—C$_6$H$_4$ |
| A.203. | 4-(4-t-C$_4$H$_9$-thiazol-2-yl)-C$_6$H$_4$ |
| A.204. | 4-(2,5-di-CH$_3$-pyrrol-1-yl)-C$_6$H$_4$ |
| A.205. | 4-(1,2,3-thidiazol-4-yl)-C$_6$H$_4$ |
| A.206. | 2-(5-Cl-1,2,3-thiadiazol-4-yl)CH$_2$O—C$_6$H$_4$ |
| A.207. | 4-(C$_6$H$_5$—NH—N=CH)—C$_6$H$_4$ |
| A.208. | 2,3-(—OCF$_2$O—)—C$_6$H$_3$ |
| A.209. | 3,4-(—OCF$_2$O—)—C$_6$H$_3$ |
| A.210. | 3-c-C$_5$H$_9$O-4-CH$_3$O—C$_6$H$_3$ |
| A.211. | 5-indanyl |

TABLE B

R¹ = heteroaryl

| No. | Meaning of R¹ |
|---|---|
| B.1. | 2-pyridyl |
| B.2. | 6-methyl-2-pyridyl |
| B.3. | 3-Cl-5-CF$_3$-2-pyridyl |
| B.4. | 4,6-(CH$_3$)$_2$—2-pyridyl |
| B.5. | 5-CN-6-CH$_3$S-2-pyridyl |
| B.6. | 3-pyridyl |
| B.7. | 6-Br-3-pyridyl |
| B.8. | 4-pyridyl |
| B.9. | 2,6-Cl$_2$-4-pyridyl |
| B.10. | 2-C$_6$H$_5$S-3-pyridyl |
| B.11. | 2(4-Cl—C$_6$H$_4$)S-3-pyridyl |
| B.12. | 4-quinolinyl |
| B.13. | 4,6-Br$_2$-4-quinolinyl |
| B.14. | 2-Cl-3-quinolinyl |
| B.15. | 3-quinolinyl |
| B.16. | 6-CH$_3$O-2-Cl-3-quinolinyl |
| B.17. | 8-OH-2-quinolinyl |
| B.18. | 2-NH$_2$-4,6-Cl$_2$-5-pyrimidyl |
| B.19. | 4-NH$_2$-2,6-(CH$_3$)$_2$—5-pyrimidyl |
| B.20. | 4,6-(CH$_3$O)$_2$-2-CH$_3$S-5-pyrimidyl |
| B.21. | 2,4-(CH$_3$O)$_2$-5-pyrimidyl |
| B.22. | 2-quinoxalinyl |
| B.23. | 2-pyrryl |
| B.24. | 1-CH$_3$-2-pyrryl |
| B.25. | 3-furanyl |
| B.26. | 5-NO$_2$-furan-2-yl |
| B.27. | 1-C$_6$H$_5$-3-CH$_3$-5-Cl-pyrazolyl |
| B.28. | 1-(4-Cl—C$_6$H$_4$)-2-pyrazolyl |
| B.29. | 1-(2-Cl—C$_6$H$_4$)-5-CF$_3$-4-pyrazolyl |
| B.30. | 1-(3-CH$_3$—C$_6$H$_4$)-5-CF$_3$-4-pyrazolyl |
| B.31. | 3-C$_2$H$_5$OCO-5-pyrazolyl |
| B.32. | 1-(4-Br—C$_6$H$_4$)-2-pyrrolyl |
| B.33. | 1-(4-CH$_3$O—C$_6$H$_4$)-3-pyrrolyl |
| B.34. | 1,2,5-trimethylpyrrolyl |
| B.35. | 1-(2,3,4-Cl$_3$—C$_6$H$_2$)-3-pyrrolyl |
| B.36. | 1-(2,4-Cl$_2$—C$_6$H$_3$)-3-pyrrolyl |
| B.37. | 1-(2-NO$_2$-4-Cl—C$_6$H$_3$)-3-pyrrolyl |
| B.38. | 3-C$_3$H$_7$-5-isoxazolyl |
| B.39. | 3-indolyl |
| B.40. | 1-CH$_3$-2-Cl-3-indolyl |
| B.41. | 4-Cl-5-nitro-2-benzothiophenyl |
| B.42. | 5-CH$_3$-4-imidazolyl |
| B.43. | 2-(4-CH$_3$O—C$_6$H$_4$)-4-oxazolyl |

TABLE B-continued $R^1$ = heteroaryl

| No. | Meaning of $R^1$ |
|---|---|
| B.44. | 1-(2,6-$(CH_3)_2$—$C_6H_3$)-pyrrolyl |
| B.45. | 2-thiazolyl |
| B.46. | 1-(4-Cl-$C_6H_4$)-3-pyrrolyl |
| B.47. | 3-(4-t$C_4H_{9}$-$C_6H_4$)-5-isoxazolyl |
| B.48. | 3-$C_6H_5$-5-isoxazolyl |
| B.49. | 1-$CH_3$-4-pyrazolyl |
| B.50. | 1-(4-Cl—$C_6H_4$)-5-$CH_3$-4-pyrazolyl |
| B.51. | 1-(4-F—$C_6H_4$)-5-$CH_3$-4-pyrazolyl |
| B.52. | 1-(4-Cl—$C_6H_4$)-3-$CH_3$-4-pyrazolyl |
| B.53. | 1-(4-Br—$C_6H_4$)-4-pyrazolyl |
| B.54. | 1-(4-Cl—$C_6H_4$)3,5-$(CH_3)$2-4-pyrazolyl |
| B.55. | 1-(4-$CH_3O$—$C_6H_4$)-5-$CF_3$-4-pyrazolyl |
| B.56. | 1-$C_6H_5$-4-pyrazolyl |
| B.57. | 1-(4-Cl—$C_6H_4$)-4-pyrazolyl |
| B.58. | 1-($C_6H_5$-S—$CH_3$)-4-pyrazolyl |
| B.59. | 2-$C_6H_5$-4-oxazolyl |
| B.60. | 2-(4-Cl—$C_6H_5$)-4-oxazolyl |
| B.61. | 4-$CH_3C_6H_4$-4-oxazolyl |
| B.62. | 4-$CH_3$-5-$C_6H_5$-3-isoxazolyl |
| B.63. | 3-(4-Cl—$C_6H_4$)-5-isoxazolyl |
| B.64. | 3-i-$C_3H_7$-5-isoxazolyl |
| B.65. | 3-t-$C_4H_{9\text{-}5\text{-isoxazolyl}}$ |
| B.66. | 3-sec-$C_4H_{9\text{-}5\text{-isoxazolyl}}$ |
| B.67. | 3-(2-$CH_3$—$C_3H_6$)-5-isoazolyl |
| B.68. | 3-t$C_4H_{9\text{-}5\text{-}C_6H_5}$-4-isoxazolyl |
| B.69. | 4-$CH_3$-5-(4-$CF_3$—$C_6H_4$)-3-isoxazolyl |
| B.70. | 3-thiophenyl |
| B.71. | 5-$CH_3$-2-thiophenyl |
| B.72. | 3-$CH_3$-2-thiophenyl |
| B.73. | 5-nitro-2-thiophenyl |
| B.74. | 5-Cl-2-thiophenyl |
| B.75. | 5-(4-F—$C_6H_4$)-2-thiophenyl |
| B.76. | 5-(4-Cl—$C_6H_4$)-2-thiophenyl |
| B.77. | 5-Br-2-thiophenyl |
| B.78. | 4,5-$Cl_2$-3-thiophenyl |
| B.79. | 2,5-$Br_2$-3-thiophenyl |
| B.80. | S-$NO_2$-3-thiophenyl |
| B.81. | 4-$CH_3$-5-imidazolyl |
| B.82. | 1-$C_6H_5CH_2$-2-imidazolyl |
| B.83. | 2-$(CH_3)_2$N-5-thiazolyl |
| B.84. | 2-(4-Cl—$C_6H_4$)-4-thiazolyl |
| B.85. | 5-$CH_3COCH_2$-2-furyl |
| B.86. | 3-Br-5-$CH_3$-2-benzo-b-thiophenyl |
| B.87. | 3,6-$Cl_2$-2-benzo-b-thiophenyl |
| B.88. | 2-$NH_2$-3-CN-4-Cl-thiophenyl |
| B.89. | 1-t-$C_4H_{9\text{-}4\text{-pyrazolyl}}$ |

The 2-oxopyroles I and their agriculturally useful salts are suitable for use as herbicides. The herbicidal compositions comprising I allow very effective control of vegetation on non-crop areas. They act against broad-leaved weeds and grass weeds in crops such as wheat, rice, maize, soybean and cotton without causing any significant damage to the crop plants. This effect is mainly observed at low rates of application.

Depending on the application method used in each case, the compounds I, or herbicidal compositions comprising them, can additionally be employed in a further number of crop plants for eliminating undesirable plants. Examples of suitable crops are the following:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N. rustica), Olea europaea, Oryza sativa , Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, vicia faba, Vitis vinifera and Zea mays.

In addition, the compounds I may also be used in crops which tolerate the action of herbicides owing to breeding, including genetic engineering methods.

Moreover, the 2-oxopyrroles I are also suitable for the desiccation and/or defoliation of plants.

As desiccants, they are suitable, in particular, for desiccating the aerial parts of crop plants such as potatoes, oilseed rape, sunflowers and soybeans. This allows completely mechanical harvesting of these important crop plants.

Also of economic interest is the facilitation of harvesting, which is made possible by dehiscence, or reduction of the adherence to the tree, both concentrated over a period of time, in citrus fruit, olives or other species and varieties of pomaceous fruit, stone fruit and nuts. The same mechanism, ie. promotion of the formation of abscission tissue between fruit or leaf and shoot of the plants, is also important for readily controllable defoliation of useful plants, in particular cotton.

Moreover, shortening the period within which the individual cotton plants mature results in improved fiber quality after harvesting.

According to the invention, the compounds of the formula I are also suitable for the control of animal pests from the classes of the insects, arachnids and nematodes. They can be used for controlling animal pests in crop protection and in the sectors of hygiene, protection of stored products and in the veterinary sector. They are particularly suitable for controlling the following animal pests:

Insects from the order of the lepidopterons (Lepidoptera), for example Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis, beetles (Coleoptera), e.g. Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and Sitophilus granaria, dipterons (Diptera), e.g. Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura rassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa, thrips (Thysanoptera), e.g. Frankliniella fusca, Frankliniella occidentalis, Frankliniella tritici, Scirtothrips citri, Thrips oryzae, Thrips palmi and Thrips tabaci, hymenopterons (Hymenoptera), e.g. Athalia rosae, Atta cephalotes, Atta sexdens, Atta texana, Hoplocampa minuta, Hoplocampa testudinea, Monomorium pharaonis, Solenopsis geminata and Solenopsis invicta, heteropterons (Heteroptera), e.g. Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis and Thyanta perditor, homopterons (Homoptera), e.g. Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum and Viteus vitifolii, termites (Isoptera), e.g. Calotermes flavicollis, Leucotermes flavipes, Reticulitermes lucifugus and Termes natalensis, orthopterons (Orthoptera), e.g. Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus, Arachnoidea such as arachnids (Acarina), e.g. Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius and Tetranychus urticae, nematodes such as root ball nematodes, e.g. Meloidogyne hapla, Meloidogyne incognita, Meloidogyne javanica, cyst-forming nematodes, e.g. Globodera rostochiensis, Heterodera avenae, Heterodera glycines, Heterodera schachtii, Heterodera trifolii, stem and leaf nematodes, e.g. Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivius, Tylenchorhynchus claytoni, Tylenchorhynchus dubius, Pratylenchus neglectus, Pratylenchus penetrans, Pratylenchus curvitatus and Pratylenchus goodeyi.

The compounds I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or pouring. The use forms depend on the intended aims; in any case, they should guarantee a very fine distribution of the active compounds according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the 2-oxopyrroles, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active compounds together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight, of at least one active compound. The active compounds are employed in a purity of from 90% to 100%, preferably 95% to 100% (according to the NMR spectrum).

The formulation examples which follow illustrate the preparation of such products:

I. 20 parts by weight of a compound of the formula I are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of a compound of the formula I are dissolved in a mixture composed of 40 parts by weight of cyclohexanone, 30 parts by weight of isobutanol, 20 parts by weight of the adduct of 7 mol of ethylene oxide to 1 mol of isooctyl phenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of a compound of the formula I are dissolved in a mixture composed of 25 parts by weight of cyclohexanone, 65 parts by weight of a mineral-oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of a compound of the formula I are mixed thoroughly with 3 parts by weight of sodium diisobutyl-naphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of a compound of the formula I are mixed with 97 parts by weight of finely divided kaolin. This gives a dust which comprises 3% by weight of the active compound.

VI. 20 parts by weight of a compound of the formula I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of a compound of the formula I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of a compound of the formula I is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The active compounds I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active compounds reach the leaves of undesirable plants growing underneath, or the bare soil surface (post-directed, lay-by).

The rates of application of active compound I are from 0.001 to 3.0, preferably 0.01 to 1.0, kg/ha of active substance (a.s.), depending on the control target, the season, the target plants and the growth stage.

To widen the spectrum of action and to achieve synergistic effects, the 2-oxopyrroles I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-CF$_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

EXAMPLE

Preparation of Ethyl E/Z-4-(2-ethylbenzylidene)-2-methyl-5-oxo-4,5-dihydropyrrole-3-carboxylate A solution of 1.5 g (0.009 mol) of ethyl 2-methyl-5-oxo-4,5-dihydropyrrole-3-carboxylate and 2.6 g (0.02 mol) of 2-ethylbenzaldehyde in 20 ml of ethanol was stirred in the presence of a few drops of HCl at room temperature.

The mixture was then concentrated and the resulting residue was chromatographed over silica gel. This gave successively 0.5 g (19%) of ethyl Z-4-(2-ethylbenzylidene)-2-methyl-5-oxo-4,5-dihydropyrrole-3-carboxylate (1H-NMR (DMSO) 8.14 ppm (=CH—Ph)) and 0.37 g (14%) of ethyl E-4-(2-ethylbenzylidene)-2-methyl-5-oxo-4,5-dihydropyrrole-3-carboxylate (1H-NMR (DMSO) 7.45 ppm (=CH—Ph)).

The compounds listed in Tables 1 to 9 below were prepared in a similar manner.

TABLE 1

A = COOCH$_3$, R$^2$ = CH$_3$

| No. | Meaning of R$^1$ | m.p. (° C.) |
|---|---|---|
| 1. | C$_6$H$_5$ | 201 (Z) |
| 2. | 1-naphthyl | 227 (Z) |
| 3. | 2-CH$_3$—C$_6$H$_4$ | 178 (Z) |
| 4. | 3-CH$_3$—C$_6$H$_4$ | 192 (Z) |
| 5. | 4-CH$_3$—C$_6$H$_4$ | 207 (Z) |
| 6. | 2,4-(CH$_3$)$_2$—C$_6$H$_3$ | 202 (Z) |
| 7. | 3,4-(CH$_3$)$_2$—C$_6$H$_3$ | 214 (Z) |
| 8. | 2,4,6-(CH$_3$)$_3$—C$_6$H$_2$ | 227 (Z) |
| 9. | 2-C$_2$H$_5$—C$_6$H$_4$ | 120 (Z) |
| 10. | 4-t-C$_4$H$_9$—C$_6$H$_4$ | 160 (Z) |
| 11. | 2-Cl—C$_6$H$_4$ | 196 (Z) |
| 12. | 4-Cl—C$_6$H$_4$ | 192 (Z) |
| 13. | 3-Cl—C$_6$H$_4$ | 202 (Z) |
| 14. | 3,5-(Cl)$_2$—C$_6$H$_3$ | 248 E:Z 35:65) |
| 15. | 2,4-(Cl)$_2$—C$_6$H$_3$ | 230 (Z) |
| 16. | 2,3-(Cl)$_2$—C$_6$H$_3$ | 244 (Z) |
| 17. | 3,4-(Cl)$_2$—C$_6$H$_3$ | 216 (Z) |

TABLE 1-continued

A = COOCH$_3$, R$^2$ = CH$_3$

| No. | Meaning of R$^1$ | m.p. (° C.) |
|---|---|---|
| 18. | 2-Cl-4-F—C$_6$H$_3$ | 225 (Z) |
| 19. | 2-Cl-6-F—C$_6$H$_3$ | 178 (Z) |
| 20. | 3-Cl-6-NO$_2$—C$_6$H$_3$ | 268 (Z) |
| 21. | 2-Br—C$_6$H$_4$ | 212–214 (Z) |
| 22. | 2-CF$_3$—C$_6$H$_4$ | 145–150 (Z) |
| 23. | 4-CF$_3$—C$_6$H$_4$ | 203–204 (Z) |
| 24. | 2,5-(CF$_3$)$_2$—C$_6$H$_3$ | 206 (Z) |
| 25. | 4-CH$_3$O—C$_6$H$_4$ | 148 (Z) |
| 26. | 3,5-(CH$_3$O)$_2$—C$_6$H$_3$ | 188 (Z) |
| 27. | 2-C$_2$H$_5$O—C$_6$H$_4$ | 172 (Z) |
| 28. | 2-OH—C$_6$H$_4$ | 198 (Z) |
| 29. | 4-CH$_2$=CH—CH$_2$O—C$_6$H$_4$ | 180 (Z) |
| 30. | 2-F—C$_6$H$_4$ | 178 (Z) |
| 31. | 4-F—C$_6$H$_4$ | 177 (Z) |
| 32. | 2,4-F$_2$—C$_6$H$_4$ | 166–167 (Z) |
| 33. | 2,6-F$_2$—C$_6$H$_4$ | 203 (Z) |
| 34. | 2-Br-4-F—C$_6$H$_3$ | 237 (Z) |
| 35. | 4-CN—C$_6$H$_4$ | 255 (Z) |
| 36. | 2-CN—C$_6$H$_4$ | 223 (Z) |
| 37. | 2-NO$_2$—C$_6$H$_4$ | 234 (Z) |
| 38. | 2-(2-Cl—C$_6$H$_4$)CH$_2$O—C$_6$H$_4$ | 165 (Z) |
| 39. | 2-(2-CH$_3$—C$_6$H$_4$)CH$_2$O—C$_6$H$_4$ | 158 (Z) |
| 40. | 2-(3-CH$_3$—C$_6$H$_4$)CH$_2$O—C$_6$H$_4$ | 120–128 (Z) |
| 41. | 2-C$_6$H$_4$—CH$_2$O—C$_6$H$_4$ | 176 (Z) |
| 42. | 4-CH$_3$CONH—C$_6$H$_4$ | 260 (Z) |
| 43. | 4-CH$_3$ON=C—C$_6$H$_4$ | 190 (Z) |
| 44. | 4-CH≡C-CH$_2$O—C$_6$H$_4$ | 179 (Z) |
| 45. | 2-SO$_3$H-4-Cl—C$_6$H$_3$ | 318 (Z) |
| 46. | 2-CH$_3$S—C$_6$H$_4$ | 179 |
| 47. | 2-CF$_3$S—C$_6$H$_4$ | 102—123 E:Z 50:50 |
| 48. | 3,5-difluorophenyl | 175 (E:Z 30:70) |
| 49. | 3,5-OCH$_3$—C$_6$H$_3$ | 217 (Z) |
| 50. | 3,5-Br$_2$—C$_6$H$_3$ | 248–250 (Z) |
| 51. | 2-F-4-Cl—C$_6$H$_3$ | 200 (Z) |
| 52. | 2-F-4-Cl-5-OCH(CH$_3$)$_2$—C$_6$H$_2$ | 206 (Z) |
| 53. | 2-(OCH$_2$CO—NH—C$_6$H$_5$)—C$_6$H$_4$ | 206–208 (Z) |
| 54. | 2-OCH$_2$CCH-C$_6$H$_4$ | 173–175 (Z) |
| 55. | 2-Cl-4-F-5-(1-methyl-4-Cl-difluoromethoxy-pyrazol-3-yl)—C$_6$H$_2$ | 169–170 (Z) |
| 56. | 2,5-F$_2$—C$_6$H$_3$ | oil (Z) |
| 57. | 2-OCHF$_2$—CHF$_2$—C$_6$H$_4$ | 135–137 (Z) |
| 58. | 2-OCF$_2$H—C$_6$H$_4$ | 170 (Z) |
| 59. | 2,6-(OCH$_3$)$_2$—C$_6$H$_3$ | 182 (Z) |
| 60. | 2-COOCH$_3$—C$_6$H$_4$ | 189–191 (Z) |
| 61. | 2-OCF$_3$—C$_6$H$_4$ | 150–154 (Z) |
| 62. | 2-Cl-6-SCH$_3$—C$_6$H$_3$ | 199 (Z) |
| 63. | 2,5-Cl$_2$—C$_6$H$_3$ | 268–269 (Z) |
| 64. | 2-Cl-6-OCH$_3$—C$_6$H$_3$ | 211–212 (Z) |
| 65. | 2-OCH$_2$—CH=CH(CH$_3$)—C$_6$H$_4$ | 123–124 (Z) |
| 66. | 2,6-Cl$_2$—C$_6$H$_3$ | 118–119 (Z) |
| 67. | 2,6-(CH$_3$S)$_2$—C$_6$H$_3$ | 156–157 (Z) |
| 68. | 2-SCH$_3$-3-Cl—C$_6$H$_3$ | 193–195 (Z) |
| 69. | 2-SCH$_3$-6-F—C$_6$H$_3$ | |

TABLE 2

A = COOCH$_2$CH$_3$, R$^2$ = CH$_3$

| No. | Meaning of R$^1$ | m.p. (° C.) |
|---|---|---|
| 1. | C$_6$H$_5$ | 179 (Z) |
| 2. | 2-CH$_3$—C$_6$H$_4$ | 165 (Z) |
| 3. | 4-CH$_3$—C$_6$H$_4$ | 195 (Z) |
| 4. | 2,4-(CH$_3$)$_2$—C$_6$H$_3$ | 180 (Z) |
| 5. | 3,4-(CH$_3$)$_2$—C$_6$H$_3$ | 223 (Z) |
| 6. | 2,4,6-(CH$_3$)$_3$—C$_6$H$_2$ | 140 (Z) 173 (E) |
| 7. | 4-t-C$_4$H$_9$—C$_6$H$_4$ | 132 (Z) 132 (E:Z 75:25) |

TABLE 2-continued $A = COOCH_2CH_3, R^2 = CH_3$

| No. | Meaning of $R^1$ | m.p. (° C.) |
|---|---|---|
| 8. | 2-Cl—$C_6H_4$ | 196 (Z) |
| 9. | 4-Cl—$C_6H_4$ | 193 (Z) |
| 10. | 5-Cl—$C_6H_4$ | 172 (Z) |
| 11. | 3,5-$(Cl)_2$—$C_6H_3$ | 208 (Z) |
| | | 202 (E:Z 60:40) |
| 12. | 2,4-$(Cl)_2$—$C_6H_3$ | 235 (Z) |
| 13. | 2,3-$(Cl)_2$—$C_6H_3$ | 230 (Z) |
| 14. | 3,4-$(Cl)_2$—$C_6H_3$ | 230 (Z) |
| 15. | 2-Cl-4-F—$C_6H_3$ | 231 (Z) |
| 16. | 2-Cl-6-F—$C_6H_3$ | 157 (Z) |
| 17. | 2-Cl-5-$NO_2$—$C_6H_3$ | 238 (Z) |
| 18. | 3-Cl-6-$NO_2$—$C_6H_3$ | 235 (Z) |
| 19. | 2-Br—$C_6H_4$ | 195 (Z) |
| 20. | 2-$CF_3$—$C_6H_4$ | 131–135 (Z) |
| 21. | 4-$CF_3$—$C_6H_4$ | 206 (Z) |
| 22. | 4-$CH_2$=CH—$CH_2O$—$C_6H_4$ | 148 (Z) |
| 23. | 2-Br-4-F—$C_6H_3$ | 215 (Z) |
| 24. | 4-CN—$C_6H_4$ | 238 (Z) |
| 25. | 2-$NO_2$—$C_6H_4$ | 200 (Z) |
| | | 164 (E:Z 85:15) |
| 26. | 2-(2-Cl—$C_6H_4$)$CH_2O$—$C_6H_4$ | 180 (Z) |
| 27. | 4-$CH_3CONH$—$C_6H_4$ | 210 (Z) |
| 28. | 4-$CH_3ON$=C—$C_6H_4$ | 192 (Z) |
| 29. | 4-CH≡C—$CH_2O$—$C_6H_4$ | 183 (Z) |
| 30. | 2-$SO_3H$-4-Cl—$C_6H_3$ | 357 (decomp.) (Z) |

TABLE 3

$A = COOC_2H_5, R^2 = CH_2CH_2CH_3$

| No. | Meaning of $R^1$ | m.p. (° C.) |
|---|---|---|
| 1. | $C_6H_5$ | 134 (Z) |
| 2. | 2-$CH_3$—$C_6H_4$ | 121.5 (Z) |
| 3. | 3-$CH_3$—$C_6H_4$ | 140 (Z) |
| 4. | 4-$CH_3$—$C_6H_4$ | 176 (Z) |
| 5. | 2,4-$(CH_3)_2$—$C_6H_3$ | 159 (Z) |
| 6. | 2-Cl—$C_6H_4$ | 129 (Z) |
| 7. | 2-Cl-4-F—$C_6H_3$ | 154 (Z) |
| 8. | 2-Cl-6-F—$C_6H_3$ | 127–129 (Z) |
| 9. | 2-Cl-5-$NO_2$—$C_6H_3$ | 193 (Z) |

TABLE 4

$A = COCCH_3, R^2 = CH_2CH_3$

| No. | Meaning of $R^1$ | m.p. (° C.) |
|---|---|---|
| 1. | $C_6H_5$ | 158–159 (Z) |
| 2. | 2-$CH_3$—$C_6H_4$ | 175–176 (Z) |
| 3. | 2-$C_2H_5$—$C_6H_4$ | oil (E) |
| | | 126–128 (Z) |
| 4. | 2-Cl—$C_6H_4$ | 178 (Z) |
| 5. | 2-Cl-4-F—$C_6H_3$ | 221 (Z) |
| 6. | 2-Cl-6-F—$C_6H_3$ | 184 (Z) |
| 7. | 2-Br—$C_6H_4$ | 185 (Z) |
| 8. | 2-$CF_3$—$C_6H_4$ | 142–145 (Z) |
| 9. | 2-F—$C_6H_4$ | 169 (Z) |
| 10. | 4-F—$C_6H_4$ | 208 (Z) |
| 11. | 2-Br-4-F—$C_6H_3$ | 220 (Z) |
| 12. | 2-F-4-Cl—$C_6H_3$ | 190 (Z) |
| 13. | 2-F-4-Cl-5-$(OCH(CH_3)_2$—$C_6H_2$ | 188 (Z) |
| 14. | 2-Cl-4-F-5-(1-methyl-4-Cl-difluoromethoxy-pyrazol-3-yl)-$C_6H_2$ | 173–175 (Z) |

TABLE 5

$A = CONH_2, R^2 = CH_3$

| No. | Meaning of $R^1$ | m.p. (° C.) |
|---|---|---|
| 1. | 2-Cl—$C_6H_4$ | 253 (Z) |
| 2. | 2-Cl-6-F—$C_6H_3$ | 208–211 (Z) |
| 3. | 2-F—$C_6H_4$ | 200 (decomp.) (Z) |
| 4. | 2-Br-4-F—$C_6H_3$ | 248–249 (Z) |

TABLE 6

| No. | Meaning of $R^1$ | Meaning of $R^2$ | Meaning of A | m.p. (° C.) |
|---|---|---|---|---|
| 1. | 2-$CH_3$—$C_6H_4$ | $CH_3$ | COO-t-$C_4H_9$ | 149–151 (Z) |
| 2. | 2-Cl—$C_6H_4$ | $CH_3$ | COO-t-$C_4H_9$ | 175–176 (Z) |
| 3. | 2-Cl-6-F—$C_6H_3$ | $CH_3$ | COO-t-$C_4H_9$ | 75–78 (Z) |
| 4. | 2-Cl-6-F—$C_6H_3$ | cyclo-$C_3H_5$ | $COOCH_3$ | MH+ 304 |
| 5. | 2-Cl-6-F—$C_6H_3$ | cyclo-$C_3H_5$ | $COOC_2H_5$ | MH+ 318 |

Furthermore, the compounds below, in which $R^1$ is a heteroaryl radical, were prepared.

TABLE 7

$A = COOCH_3; R^2 = CH_3$

| No. | Meaning of $R^1$ | m.p. (° C.) |
|---|---|---|
| 1. | 3-pyridyl | 180 (Z) |
| 2. | 4-pyridyl | 182–184 (Z) |
| 3. | 4,6-$(CH_3O)_2$-2-$CH_3S$-5-pyrimidyl | 214–216 (Z) |
| 4. | 2-pyrryl | 217 (Z) |
| 5. | 1-$CH_3$-2-pyrryl | 280–282 (Z) |
| 6. | 3-furanyl | 200–201 (Z) |
| 7. | 5-$NO_2$-furan-2-yl | 235 (Z) |
| 8. | 1-(2,4-$Cl_2$—$C_6H_3$)-3-pyrrolyl | 202 (Z) |
| 9. | 3-$C_3H_7$-2-isoxazolyl | |
| 10. | 3-indolyl | 245–248 (Z) |
| 11. | 1-$CH_3$-4-pyrazolyl | 196 (Z) |
| 12. | 1-(4-Cl—$C_6H_4$)-4-pyrazolyl | 273–275 (Z) |
| 13. | 2-$C_6H_5$-4-oxazolyl | 260 (Z) |
| 14. | 3-(4-Cl—$C_6H_4$)-5-isoxazolyl | 245–246 (Z) |
| 15. | 3-i-$C_3H_7$-5-isoxazolyl | 210–211 (Z) |
| 16. | 3-thiophenyl | 206 (Z) |
| 17. | 5-$CH_3$-2-thiophenyl | 234 (Z) |
| 18. | 3-$CH_3$-2-thiophenyl | 248 (Z) |
| 19. | 5-Cl-2-thiophenyl | 219 (Z) |
| 20. | 2,5-$Br_2$-3-thiophenyl | 236–238 (Z) |
| 21. | 4-$CH_3$-5-imidazolyl | 250 (decomp.) (Z) |
| 22. | 2-$(CH_3)_2N$-5-thiazolyl | 252–255 (Z) |
| 23. | 3-Br-5-$CH_3$-2-benzo-b-thiophenyl | 240 (Z) |
| 24. | 2-furyl | 180 (Z) |
| 25. | 2 hydroxyquinolyl | 291 (Z) |
| 26. | 2-thiophenyl | 223–225 (Z) |
| 27. | 4-Br-2-thiophenyl | 247 (Z) |
| 28. | 3-Br-2-thiophenyl | 257–258 (Z) |
| 29. | 4-CN-2-thiophenyl | 291–293 (Z) |

TABLE 8

$A = COOC_2H_5, R^2 = CH_3$

| No. | Meaning of $R^1$ | m.p. (° C.) |
|---|---|---|
| 1. | 3-pyridyl | 210 (Z) |
| 2. | 4-pyridyl | 178–180 (Z) |
| 3. | 4,6-$(CH_3O)_2$-2-$CH_3S$-5-pyrimidyl | 226 (Z) |
| 4. | 2-pyrryl | 197 (Z) |
| 5. | 5-$NO_2$-furanyl | 240 (Z) |
| 6. | 1,2,5-trimethylpyrrolyl | 181 (Z) |
| 7. | 3-$C_3H_7$-2-isoxazolyl | 259 (Z) |

TABLE 8-continued

A = COOC$_2$H$_5$, R$^2$ = CH$_3$

| No. | Meaning of R$^1$ | m.p. (° C.) |
|---|---|---|
| 8. | 1-CH$_3$-4-pyrazolyl | 213 (Z) |
| 9. | 1-(4-Cl—C$_6$H$_4$)-4-pyrazolyl | 258 (Z) |
| 10. | 2-C$_6$H$_5$-4-oxazolyl | 252 (Z) |
| 11. | 3-(4-Cl-C$_6$H$_4$)-5-isoxazolyl | 273 (Z) |
| 12. | 3-i-C$_3$H$_7$-5-isoxazolyl | 226 (Z) |
| 13. | 4-CH$_3$-5-imidazolyl | 114 (Z) |
| 14. | 2-(CH$_3$)-$_2$N-5-thiazolyl | 284 (Z) |
| 15. | 2-furyl | 218 (Z) |
| 16. | 2-hydroxyquinolyl | >295 (Z) |

TABLE 9

| No. | Meaning of R$^1$ | R$^2$ | Meaning of A | m.p. (° C.) |
|---|---|---|---|---|
| 1. | 3-C$_3$H$_7$-5-isoxazolyl | CH$_3$ | CONH$_2$ | 149–151 (Z) |

Examples of the Herbicidal Activity

For the post-emergence treatment, the test plants were first grown to a height of 3 to 15 cm, depending on the plant habit, and only then treated with the active compounds which had been suspended or emulsified in water. For this purpose, the test plants were either sown directly and grown in the same containers, or they were first grown separately as seedlings and transplanted into the test containers a few days prior to treatment.

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the above-ground parts, and 0 means no damage, or normal course of growth.

The results are shown in the tables below:

TABLE 10

Application rate in each case 3.0 g of a.s./ha

| | | Efficacy against | | |
|---|---|---|---|---|
| No. | Compound tested | ABUTH | SETIT | SINAL |
| 1 | Table 1, No. 1 | | 90 | 100 |
| 2 | Table 1, No. 3 | 100 | 95 | 100 |
| 3 | Table 1, No. 9 | | 90 | 100 |
| 4 | Table 1, No. 13 | | 100 | 100 |
| 5 | Table 1, No. 18 | | 100 | 100 |
| 6 | Table 1, No. 19 | 95 | 100 | 100 |

ABUTH: velvet leaf (*Abuthilon theophrasti*)
SETIT: foxtail millet (*Setaria italica*)
SINAL: white mustard (*Sinapis alba*)

We claim:

1. A method of protecting crop plants which comprises treating the crop plants or their environment or both with an amount of from 0.001 to 3 kg/ha of a 2-oxopyrrole compound of formula I

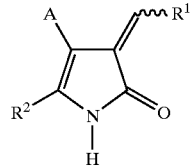

(I)

or an agriculturally useful salt thereof, wherein
R$^1$ is an aryl which is unsubstituted or carries one to five substituents, and which ring is optionally fused with a cyclic radical selected from the group of: phenyl, C$_3$–C$_6$-carbocycles and 5- and 6-membered heterocycles, to form a bicyclic system, wherein the fused-on cyclic radical optionally carries from one to three substituents;
R$^2$ is C$_1$–C$_6$-alkyl, C$_3$–C$_7$-cycloalkyl or C$_1$–C$_6$-alkylaryl; or is an aryl or heteroaryl ring which is unsubstituted or carries from one to three substituents;
A is COOR$^3$ or CONR$^3$R$^4$, where R$^3$ and R$^4$ independently of one another are hydrogen, C$_1$–C$_6$-alkyl, C$_2$–C$_6$-alkenyl, C$_3$–C$_7$-cy-cloalkyl or C$_1$–C$_6$-alkylaryl, which may be partially or fully halogenated or may carry one to three substituents selected from the group consisting of C$_1$–C$_4$-alkoxy, C$_1$–C$_4$-haloalkoxy, C$_1$–C$_4$-alkylthio, C$_3$–C$_7$-cycloalkyl, C$_5$–C$_7$-cycloalkenyl; and
wherein the substituents referred to in the definition of R$^1$ and R$^2$ are independently selected from the group consisting of:
halogen, cyano, nitro, hydroxyl, mercapto, thiocyanato, carboxyl, amino, C$_1$–C$_6$-alkyl, C$_1$–C$_6$-cyanoalkyl, C$_2$–C$_6$-alkenyl, C$_1$–C$_6$-alkoxy-C$_2$–C$_6$-alkenyl, C$_3$–C$_6$-alkynyl, C$_1$–C$_6$-alkoxy-C$_3$–C$_6$-alkynyl, C$_3$–C$_6$-alkynyl-C$_1$–C$_6$-alkoxy, C$_3$–C$_7$-cycloalkyl, C$_1$–C$_6$-alkyl-C$_3$–C$_7$-cycloalkyl, C$_1$–C$_6$-alkoxy-C$_3$–C$_7$-cycloalkyl, C$_3$–C$_7$-cycloalkyloxy, C$_3$–C$_7$-cyanocycloalkyloxy, C$_1$–C$_6$-alkyl-C$_3$–C$_7$-cycloalkyloxy, C$_3$–C$_7$-halocycloalkyl, C$_3$–C$_7$-cyanocycloalkyl, C$_3$–C$_7$-halocycloalkyloxy, C$_5$–C$_7$-cycloalkenyl, C$_1$–C$_6$-alkyl-C$_5$–C$_7$-cycloalkenyl, C$_1$–C$_6$-alkoxy-C$_5$–C$_7$-cycloalkenyl, C$_5$–C$_7$-cyanocycloalkenyl, C$_5$–C$_7$-halocycloalkenyl, C$_1$–C$_6$-alkoxy-C$_1$–C$_6$-alkyl, C$_1$–C$_6$-haloalkyl, C$_2$–C$_6$-haloalkenyl, C$_3$–C$_6$-haloalkynyl, C$_2$–C$_6$-cyanoalkenyl, C$_3$–C$_6$-cyanoalkynyl, C$_1$–C$_6$-alkoxy, C$_1$–C$_6$-cyanoalkoxy, C$_1$–C$_6$-haloalkoxy, C$_2$–C$_6$-alkenyloxy, C$_2$–C$_6$-cyanoalkenyloxy, C$_2$–C$_6$-haloalkenyloxy, C$_2$–C$_6$-alkynyloxy, C$_1$–C$_6$-alkylthio, C$_1$–C$_6$-cyanoalkylthio, C$_1$–C$_6$-haloalkylthio, C$_1$–C$_6$-alkoxy-C$_1$–C$_6$-alkylthio, C$_1$–C$_6$-alkoxycarbonyl, C$_1$–C$_6$-alkylcarbonyl, C$_1$–C$_6$-alkylcarboxy-C$_1$–C$_6$-alkyl, C$_1$–C$_6$-alkylcarbonyl-C$_1$–C$_6$-alkyl, C$_1$–C$_6$-alkylcarbonylamino, arylcarbonylamino, arylsulfinyl, arylsulfonyl, heteroarylsulfinyl, heteroarylsulfonyl, aryl-C$_1$–C$_6$-alkyl, aryl-C$_2$–C$_6$-alkenyl, aryl-C$_3$–C$_6$-alkynyl, heteroaryl-C$_1$–C$_6$-alkyl, heteroaryl-C$_2$–C$_6$-alkenyl, heteroaryl-C$_3$–C$_6$-alkynyl, aryl-C$_1$–C$_6$-alkoxy, aryl-C$_2$–C$_6$-alkenyloxy, aryl-C$_3$–C$_6$-alkynyloxy, heteroaryl-C$_1$–C$_6$-alkoxy, heteroaryl-C$_2$–C$_6$-alkenyloxy, heteroaryl-C$_3$–C$_6$-alkynyloxy, C$_1$–C$_6$-alkylsulfinyl, C$_1$–C$_6$-alkylsulfonyl, C$_2$–C$_6$-alkenylsulfinyl, C$_2$–C$_6$-alkenylsulfonyl, C$_1$–C$_6$-alkylamino, di-C$_1$–C$_6$- alkylamino, HC=NOH, $C_1$–$C_6$-alkyl-C=NOH, HC=N—O—$C_1$–$C_6$-alkyl, HC=N—O—$C_1$–$C_6$-alkyl-aryl $C_1$–$C_6$-alkyl-C=N—O—$C_1$–$C_6$-alkyl, HC=N—O—$C_2$–$C_6$-alkenyl, $C_1$–$C_6$-alkyl-C=N—O—$C_2$–$C_6$-alkenyl, HC=N—O-aryl, $C_1$–$C_6$-alkyl-C=N—O-aryl, aryl, aryloxy, heteroaryl, heteroaryloxy, arylthio and heteroarylthio, where the cyclic substituents for their part optionally carry one to five radicals selected from the group consisting of: halogen, cyano, nitro, hydroxyl, mercapto, thiocyanato, carboxyl, amino, $C_1$–$C_6$-alkyl, $C_1$–$C_6$-cyanoalkyl, $C_2$–$C_6$-alkenyl, $C_1$–$C_6$-alkoxy-$C_2$–$C_6$-alkenyl, $C_3$–$C_6$-alkynyl, $C_1$–$C_6$-alkoxy-$C_3$–$C_6$-alkynyl, $C_3$–$C_6$-alkynyl-$C_1$–$C_6$-alkoxy, $C_3$–$C_7$-cycloalkyl, $C_1$–$C_6$-alkyl-$C_3$–$C_7$-cycloalkyl, $C_1$–$C_6$-alkoxy-$C_3$–$C_7$-cycloalkyl, $C_3$–$C_7$-cycloalkyloxy, $C_3$–$C_7$-cyanocycloalkyloxy, $C_1$–$C_6$-alkyl-$C_3$–$C_7$-cycloalkyloxy, $C_3$–$C_7$-halocycloalkyl, $C_3$–$C_7$-cyanocycloalkyl, $C_3$–$C_7$-halocycloalkyloxy, $C_5$–$C_7$-cycloalkenyl, $C_1$–$C_6$-alkyl-$C_5$–$C_7$-cycloalkenyl, $C_1$–$C_6$-alkoxy-$C_5$–$C_7$-cycloalkenyl, $C_5$–$C_7$-cyanocycloalkenyl, $C_5$–$C_7$-halocycloalkenyl, $C_1$–$C_6$-alkoxy-$C_1$–$C_6$-alkyl, $C_1$–$C_6$-haloalkyl, $C_2$–$C_6$-haloalkenyl, $C_3$–$C_6$-haloalkynyl, $C_2$–$C_6$-cyanoalkenyl, $C_3$–$C_6$-cyanoalkynyl, $C_1$–$C_6$-alkoxy, $C_1$–$C_6$-cyanoalkoxy, $C_1$–$C_6$-haloalkoxy, $C_2$–$C_6$-alkenyloxy, $C_2$–$C_6$-cyanoalkenyloxy, $C_2$–$C_6$-haloalkenyloxy, $C_2$–$C_6$-alkynyloxy, $C_1$–$C_6$-alkylthio, $C_1$–$C_6$-cyanoalkylthio, $C_1$–$C_6$-haloalkylthio, $C_1$–$C_6$-alkoxy-$C_1$–$C_6$-alkylthio, $C_1$–$C_6$-alkoxycarbonyl, $C_1$–$C_6$-alkylcarbonyl, $C_1$–$C_6$-alkylcarboxy-$C_1$–$C_6$-alkyl, $C_1$–$C_6$-alkylcarbonyl-$C_1$–$C_6$-alkyl, $C_1$–$C_6$-alkylcarbonylamino, arylcarbonylamino, arylsulfinyl, arylsulfonyl, heteroarylsulfinyl, heteroarylsulfonyl, aryl-$C_1$–$C_6$-alkyl, aryl-$C_2$–$C_6$-alkenyl, aryl-$C_3$–$C_6$-alkynyl, heteroaryl-$C_1$–$C_6$-alkyl, heteroaryl-$C_2$–$C_6$-alkenyl, heteroaryl-$C_3$–$C_6$-alkynyl, aryl-$C_1$–$C_6$-alkoxy, aryl-$C_2$–$C_6$-alkenyloxy, aryl-$C_3$–$C_6$-alkynyloxy, heteroaryl-$C_1$–$C_6$-alkoxy, heteroaryl-$C_2$–$C_6$-alkenyloxy, heteroaryl-$C_3$–$C_6$-alkynyloxy, $C_1$–$C_6$-alkylsulfinyl, $C_1$–$C_6$-alkylsulfonyl, $C_2$–$C_6$-alkenylsulfinyl, $C_2$–$C_6$-alkenylsulfonyl, $C_1$–$C_6$-alkylamino, di-$C_1$–$C_6$-alkylamino, HC=NOH, $C_1$–$C_6$-alkyl-C=NOH, HC=N—O—$C_1$–$C_6$-alkyl, HC=N—O—$C_1$–$C_6$-alkyl-aryl, $C_1$–$C_6$-alkyl-C=N—O—$C_1$–$C_6$-alkyl, HC=N—$C_2$–$C_6$-alkenyl, $C_1$–$C_6$-alkyl-C=N—$C_2$–$C_6$-alkenyl, HC=N—O-aryl, $C_1$–$C_6$-alkyl-C=N—O-aryl, aryl, aryloxy, heteroaryl, heteroaryloxy, arylthio and heteroarylthio.

2. The method of claim 1, wherein the compound of formula I is used as a herbicide.

3. The method of claim 1, wherein the compound of formula I is used as an insecticide.

4. The method of claim 1 wherein the compound of formula I is applied in an amount of from 0.01 to 1 kg/ha.

5. A method of protecting crop plants from harm caused by unwanted plants or animal pests which comprises treating the crop plants, the unwanted plants or animal pests, or their environment with an amount of from 0.001 to 3 kg/ha of a compound of formula I

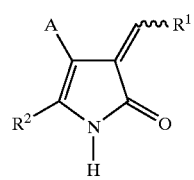

(I)

or an agriculturally useful salt thereof, wherein $R^1$ is an aryl ring which is unsubstituted or carries from one to five substituents, and which ring is optionally fused with a cyclic radical selected from the group of: phenyl, $C_3$–$C_6$-carbocycles and 5- and 6-membered heterocycles, to form a bicyclic system, wherein the fused-on cyclic radical optionally carries from one to three substituents;

$R^2$ is $C_1$–$C_6$-alkyl, $C_3$–$C_7$-cycloalkyl or $C_1$–$C_6$-alkylaryl; or is an aryl or heteroaryl ring which is unsubstituted or carries from one to three substituents;

A is $COOR^3$ or $CONR^3R^4$, where $R^3$ and $R^4$ independently of one another are hydrogen, $C_1$–$C_6$-alkyl, $C_2$–$C_6$-alkenyl, $C_3$–$C_7$-cycloalkyl or $C_1$–$C_6$-alkyl-aryl, which may be partially or fully halogenated or may carry one to three radicals selected from the group consisting of $C_1$–$C_4$-alkoxy, $C_1$–$C_4$-haloalkoxy, $C_1$–$C_4$-alkylthio, $C_3$–$C_7$-cycloalkyl and $C_5$–$C_7$-cycloalkenyl; and wherein the substituents referred to in the definition of $R^1$ and $R^2$ are independently selected from the group consisting of:

halogen, cyano, nitro, hydroxyl, mercapto, thiocyanato, carboxyl, amino, $C_1$–$C_6$-alkyl, $C_1$–$C_6$-cyanoalkyl, $C_2$–$C_6$-alkenyl, $C_1$–$C_6$-alkoxy-$C_2$–$C_6$-alkenyl, $C_3$–$C_6$-alkynyl, $C_1$–$C_6$-alkoxy-$C_3$–$C_6$-alkynyl, $C_3$–$C_6$-alkynyl-$C_1$–$C_6$-alkoxy, $C_3$–$C_7$-cycloalkyl, $C_1$–$C_6$-alkyl-$C_3$–$C_7$-cycloalkyl, $C_1$–$C_6$-alkoxy-$C_3$–$C_7$-cycloalkyl, $C_3$–$C_7$-cycloalkyloxy, $C_3$–$C_7$-cyanocycloalkyloxy, $C_1$–$C_6$-alkyl-$C_3$–$C_7$-cycloalkyloxy, $C_3$–$C_7$-halocycloalkyl, $C_3$–$C_7$-cyanocycloalkyl, $C_3$–$C_7$-halocycloalkyloxy, $C_5$–$C_7$-cycloalkenyl, $C_1$–$C_6$-alkyl-$C_5$–$C_7$-cycloalkenyl, $C_1$–$C_6$-alkoxy-$C_5$–$C_7$-cycloalkenyl, $C_5$–$C_7$-cyanocycloalkenyl, $C_5$–$C_7$-halocycloalkenyl, $C_1$–$C_6$-alkoxy-$C_1$–$C_6$-alkyl, $C_1$–$C_6$-haloalkyl, $C_2$–$C_6$-haloalkenyl, $C_3$–$C_6$-haloalkynyl, $C_2$–$C_6$-cyanoalkenyl, $C_3$–$C_6$-cyanoalkynyl, $C_1$–$C_6$-alkoxy, $C_1$–$C_6$-cyanoalkoxy, $C_1$–$C_6$-haloalkoxy, $C_2$–$C_6$-alkenyloxy, $C_2$–$C_6$-cyanoalkenyloxy, $C_2$–$C_6$-haloalkenyloxy, $C_2$–$C_6$-alkynyloxy, $C_1$–$C_6$-alkylthio, $C_1$–$C_6$-cyanoalkylthio, $C_1$–$C_6$-haloalkylthio, $C_1$–$C_6$-alkoxy-$C_1$–$C_6$-alkylthio, $C_1$–$C_6$-alkoxycarbonyl, $C_1$–$C_6$-alkylcarbonyl, $C_1$–$C_6$-alkylcarboxy-$C_1$–$C_6$-alkyl, $C_1$–$C_6$-alkylcarbonyl-$C_1$–$C_6$-alkyl, $C_1$–$C_6$-alkylcarbonylamino, arylcarbonylamino, arylsulfinyl, arylsulfonyl, heteroarylsulfinyl, heteroarylsulfonyl, aryl-$C_1$–$C_6$-alkyl, aryl-$C_2$–$C_6$-alkenyl, aryl-$C_3$–$C_6$-alkynyl, heteroaryl-$C_1$–$C_6$-alkyl, heteroaryl-$C_2$–$C_6$-alkenyl, heteroaryl-$C_3$–$C_6$-alkynyl, aryl-$C_1$–$C_6$-alkoxy, aryl-$C_2$–$C_6$-alkenyloxy, aryl-$C_3$–$C_6$-alkynyloxy, heteroaryl-$C_1$–$C_6$-alkoxy, heteroaryl-$C_2$–$C_6$-alkenyloxy, heteroaryl-$C_3$–$C_6$-alkynyloxy, $C_1$–$C_6$-alkylsulfinyl, $C_1$–$C_6$-alkylsulfonyl, $C_2$–$C_6$-alkenylsulfinyl, $C_2$–$C_6$-alkenylsulfonyl, $C_1$–$C_6$-alkylamino, di-$C_1$–$C_6$- alkylamino, HC=NOH, $C_1$–$C_6$-alkyl-C=NOH, HC=N—O—$C_1$–$C_6$-alkyl, HC=N—O—$C_1$–$C_6$-alkylaryl, $C_1$–$C_6$-alkyl-C=N—O—$C_1$–$C_6$-alkyl, HC=N—O—$C_2$–$C_6$-alkenyl, $C_1$–$C_6$-alkyl-C=N—O—$C_2$–$C_6$-alkenyl, HC=N—O-aryl, $C_1$–$C_6$-alkyl-C=N—O-aryl, aryl, aryloxy, heteroaryl, heteroaryloxy, arylthio and heteroarylthio, where the cyclic substituents for their part optionally carry one to five radicals selected from the group consisting of: halogen, cyano, nitro, hydroxyl, mercapto, thiocyanato, carboxyl, amino, $C_1$–$C_6$-alkyl, $C_1$–$C_6$-cyanoalkyl, $C_2$–$C_6$-alkenyl, $C_1$–$C_6$-alkoxy-$C_2$–$C_6$-alkenyl, $C_3$–$C_6$-alkynyl, $C_1$–$C_6$-alkoxy-$C_3$–$C_6$-alkynyl, $C_3$–$C_6$-alkynyl-$C_1$–$C_6$-alkoxy, $C_3$–$C_7$-cycloalkyl, $C_1$–$C_6$-alkyl-$C_3$–C7-cycloalkyl, $C_1$–$C_6$-alkoxy-$C_3$–$C_7$-cycloalkyl, $C_3$–$C_7$-cycloalkyloxy, $C_3$–$C_7$-cyanocycloalkyloxy, $C_1$–$C_6$-alkyl-$C_3$–$C_7$-cycloalkyloxy, $C_3$–C-7-halocycloalkyl, $C_3$–$C_7$-cyanocycloalkyl, $C_3$–$C_7$-halocycloalkyloxy, $C_5$–$C_7$-cycloalkenyl, $C_1$–$C_6$-alkyl-$C_5$–$C_7$-cycloalkenyl, $C_1$–$C_6$-alkoxy-$C_5$–$C_7$-cycloalkenyl, $C_5$–$C_7$-cyanocycloalkenyl, $C_5$–$C_7$-halocycloalkenyl, $C_1$–$C_6$-alkoxy-$C_1$–$C_6$-alkyl, $C_1$–$C_6$-haloalkyl, $C_2$–$C_6$-haloalkenyl, $C_3$–$C_6$-haloalkynyl, $C_2$–$C_6$-cyanoalkenyl, $C_3$–$C_6$-cyanoalkynyl, $C_1$–$C_6$-alkoxy, $C_1$–$C_6$-cyanoalkoxy, $C_1$–$C_6$-haloalkoxy, $C_2$–$C_6$-alkenyloxy, $C_2$–$C_6$-cyanoalkenyloxy, $C_2$–$C_6$-haloalkenyloxy, $C_2$–$C_6$-alkynyloxy, $C_1$–$C_6$-alkylthio, $C_1$–$C_6$-cyanoalkylthio, $C_1$–$C_6$-haloalkylthio, $C_1$–$C_6$-alkoxy-$C_1$–$C_6$-alkylthio, $C_1$–$C_6$-alkoxycarbonyl, $C_1$–$C_6$-alkylcarbonyl, $C_1$–$C_6$-alkylcarboxy-$C_1$–$C_6$-alkyl, $C_1$–$C_6$-alkylcarbonyl-$C_1$–$C_6$-alkyl, $C_1$–$C_6$-alkylcarbonylamino, arylcarbonylamino, arylsulfinyl, arylsulfonyl, heteroarylsulfinyl, heteroarylsulfonyl, aryl-$C_1$–$C_6$-alkyl, aryl-$C_2$–$C_6$-alkenyl, aryl-$C_3$–$C_6$-alkynyl, heteroaryl-$C_1$–$C_6$-alkyl, heteroaryl-$C_2$–$C_6$-alkenyl, heteroaryl-$C_3$–$C_6$-alkynyl, aryl-$C_1$–$_6$-alkoxy, aryl-$C_2$–$C_6$-alkenyloxy, aryl-$C_3$–$C_6$-alkynyloxy, heteroaryl-$C_1$–$C_6$-alkoxy, heteroaryl-$C_2$–$C_6$-alkenyloxy, heteroaryl-$C_3$–$C_6$-alkynyloxy, $C_1$–$C_6$-alkylsulfinyl, $C_1$–$C_6$-alkylsulfonyl, $C_2$–$C_6$-alkenylsulfinyl, $C_2$–$C_6$-alkenylsulfonyl, $C_1$–$C_6$-alkylamino, di-$C_1$–$C_6$-alkylamino, HC=NOH, $C_1$–$C_6$-alkyl-C=NOH, HC=N—O—$C_1$–$C_6$-alkyl, HC=N—O—$C_1$–$C_6$-alkyl-aryl, $C_1$–$C_6$-alkyl-C=N—O—$C_1$–$C_6$-alkyl, HC=N—O—$C_2$–$C_6$-alkenyl, $C_1$–$C_6$-alkyl-C=N—$C_2$–$C_6$-alkenyl, HC=N—O-aryl, $C_1$–$C_6$-alkyl-C=N—O-aryl, aryl, aryloxy, heteroaryl, heteroaryloxy, arylthio and heteroarylthio.

6. The method of claim 5 wherein the compound of formula I is applied in an amount of from 0.01 to 1 kg/ha.

* * * * *

UNITED STATES PATENT AND TRADEMARK OFFICE
CERTIFICATE OF CORRECTION

PATENT NO. : 6,548,451 B1
DATED : April 15, 2003
INVENTOR(S) : Wagner et al.

It is certified that error appears in the above-identified patent and that said Letters Patent is hereby corrected as shown below:

Column 26,
Line 24, "$C_3$-$C_7$-cy-cloalkyl" should be -- $C_3$-$C_7$-cycloalkyl --.

Column 27,
Line 16, "$C_l$-$C_6$" should read -- $C_1$-$C_6$- --.

Column 29,
Line 15, "$C_3$-C7-cycloalkyl" should read -- $C_3$-$C_7$-cycloalkyl --.
Line 18, "$C_3$-C-7-halocycloalkyl" should be -- $C_3$-$C_7$-halocycloalkyl --.

Signed and Sealed this

Second Day of September, 2003

JAMES E. ROGAN
*Director of the United States Patent and Trademark Office*